US011572587B2

(12) United States Patent
Murphy et al.

(10) Patent No.: US 11,572,587 B2
(45) Date of Patent: Feb. 7, 2023

(54) METHOD FOR DIAGNOSING SUBCLINICAL AND CLINICAL ACUTE REJECTION BY ANALYSIS OF PREDICTIVE GENE SETS

(71) Applicant: Icahn School of Medicine at Mount Sinai, New York, NY (US)

(72) Inventors: Barbara Murphy, Pelham Manor, NY (US); Weijia Zhang, Cresskill, NJ (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/321,885

(22) PCT Filed: Jun. 26, 2015

(86) PCT No.: PCT/US2015/038171
§ 371 (c)(1),
(2) Date: Dec. 23, 2016

(87) PCT Pub. No.: WO2015/200887
PCT Pub. Date: Dec. 30, 2015

(65) Prior Publication Data
US 2017/0137883 A1    May 18, 2017

Related U.S. Application Data

(60) Provisional application No. 62/017,784, filed on Jun. 26, 2014.

(51) Int. Cl.
| C12Q 1/6883 | (2018.01) |
| A61K 31/365 | (2006.01) |
| A61K 31/436 | (2006.01) |
| A61K 31/52 | (2006.01) |
| A61K 31/573 | (2006.01) |
| A61K 38/13 | (2006.01) |

(52) U.S. Cl.
CPC .......... *C12Q 1/6883* (2013.01); *A61K 31/365* (2013.01); *A61K 31/436* (2013.01); *A61K 31/52* (2013.01); *A61K 31/573* (2013.01); *A61K 38/13* (2013.01); *C12Q 2600/158* (2013.01)

(58) Field of Classification Search
None
See application file for complete search history.

(56) References Cited

U.S. PATENT DOCUMENTS

| 6,582,908 | B2 | 6/2003 | Fodor et al. |
| 10,308,985 | B2 | 6/2019 | Murphy et al. |
| 10,787,709 | B2 | 9/2020 | Murphy et al. |
| 10,941,446 | B2 | 3/2021 | Murphy et al. |
| 2006/0270612 | A1 | 11/2006 | Blatt et al. |
| 2007/0269827 | A1 | 11/2007 | Harley |
| 2008/0319027 | A1 | 12/2008 | Tao et al. |
| 2009/0022730 | A1 | 1/2009 | Raulf et al. |
| 2009/0191548 | A1 | 7/2009 | Berlin et al. |
| 2011/0144914 | A1 | 6/2011 | Harrington et al. |
| 2011/0171664 | A1 | 7/2011 | O'Brien |
| 2011/0189680 | A1 | 8/2011 | Keown et al. |
| 2011/0212090 | A1 | 9/2011 | Pedersen et al. |
| 2012/0003228 | A1 | 1/2012 | Smith et al. |
| 2012/0177645 | A1 | 7/2012 | Langermann et al. |
| 2012/0282696 | A1 | 11/2012 | Johnson et al. |
| 2012/0321614 | A1 | 12/2012 | Michaud et al. |
| 2013/0064835 | A1 | 3/2013 | Schmidt |
| 2013/0078633 | A1 | 3/2013 | Hutchins et al. |
| 2013/0131194 | A1 | 5/2013 | Skog et al. |
| 2013/0142728 | A1 | 6/2013 | Beaudenon-Huibregtse et al. |
| 2013/0143755 | A1 | 6/2013 | Sarwal et al. |
| 2013/0216533 | A1 | 8/2013 | Bais et al. |
| 2014/0045915 | A1 | 2/2014 | Skog et al. |
| 2014/0100124 | A1 | 4/2014 | Wylie et al. |
| 2014/0141986 | A1 | 5/2014 | Spetzler et al. |
| 2014/0329704 | A1 | 11/2014 | Melton et al. |
| 2015/0167085 | A1* | 6/2015 | Salomon ............... G16H 20/40 506/3 |
| 2017/0114407 | A1 | 4/2017 | Murphy et al. |
| 2017/0152560 | A1 | 6/2017 | Murphy et al. |
| 2018/0068057 | A1 | 3/2018 | Shin et al. |
| 2018/0356402 | A1 | 12/2018 | Fairchild et al. |
| 2019/0345556 | A1 | 11/2019 | Murphy et al. |
| 2021/0230700 | A1 | 7/2021 | Murphy et al. |
| 2022/0090197 | A1 | 3/2022 | Murphy et al. |

FOREIGN PATENT DOCUMENTS

| CN | 1518458 | 8/2004 |
| CN | 101039951 | 9/2007 |
| CN | 101360835 | 2/2009 |
| CN | 102099484 | 6/2011 |
| CN | 102119224 A | 7/2011 |
| CN | 102186987 | 9/2011 |
| CN | 102597268 | 7/2012 |
| CN | 102666581 | 9/2012 |

(Continued)

OTHER PUBLICATIONS

Shendure et al. Next-generation DNA sequencing. Nature Biotechnology 2008, vol. 26, No. 10, p. 1135-1145 (Year: 2008).*
Metzker. Sequencing technologies—the next generation. Nature Reviews Genetics 2010, vol. 11, p. 31-46 (Year: 2010).*
Schadt et al. A window into third-generation sequencing. Human Molecular Genetics, 2010, vol. 19, Review Issue 2, p. R227-R240 (Year: 2010).*
Affymetrix NetAffx Search results, pp. 1-17, accessed Apr. 8, 2021 (Year: 2021).*
Alakulppi et al., "Diagnosis of Acute Renal Allograft Rejection by Analyzing Whole Blood mRNA Expression of Lymphocyte Marker Molecules," Transplantation, Mar. 2007, 83: 791-798.
Extended European Search Report in Application No. 15812651.6, dated Jan. 3, 2018, 9 pages.

(Continued)

*Primary Examiner* — Olivia M. Wise
(74) *Attorney, Agent, or Firm* — Fish & Richardson P.C.

(57) ABSTRACT

Disclosed herein are methods for diagnosing acute cellular rejection (ACR) of an allograft by analysis of predictive gene sets and kits for practicing these methods.

13 Claims, No Drawings

Specification includes a Sequence Listing.

(56) References Cited

FOREIGN PATENT DOCUMENTS

| CN | 102712954 | 10/2012 |
|---|---|---|
| CN | 103025890 | 4/2013 |
| CN | 103421905 | 12/2013 |
| CN | 106461679 | 2/2017 |
| EP | 1374901 | 1/2004 |
| EP | 1731620 | 12/2006 |
| WO | WO 1996/039154 | 12/1996 |
| WO | WO 1997/003211 | 1/1997 |
| WO | WO 2001/081916 | 11/2001 |
| WO | WO 2004/074815 | 9/2004 |
| WO | 2007/104537 | 9/2007 |
| WO | WO 2009/143624 | 12/2009 |
| WO | WO 2010/083121 | 7/2010 |
| WO | WO 2011/127219 | 10/2011 |
| WO | WO 2011/143499 | 11/2011 |
| WO | WO 2012/174282 | 12/2012 |
| WO | WO 2013/063322 | 5/2013 |
| WO | WO 2013/063544 | 5/2013 |
| WO | WO 2013/079701 | 7/2013 |
| WO | WO 2013/079791 | 7/2013 |
| WO | WO 2014/045915 | 3/2014 |
| WO | WO 2014/071205 | 5/2014 |
| WO | WO 2017/100259 | 6/2017 |
| WO | WO 2017/147196 | 8/2017 |
| WO | WO 2017/203008 | 11/2017 |

OTHER PUBLICATIONS

Flechner et al., "Kidney Transplant Rejection and Tissue Injury by Gene Profiling of Biopsies and Peripheral Blood Lymphocytes," American Journal of Transplantation, Sep. 2004, 4: 1475-1489.

Li et al., "Identification of Common Blood Gene Signatures for the Diagnosis of Renal and Cardiac Acute Allograft Rejection," PLOS One, Dec. 2013, 8: e82153.

International Search Report and Written Opinion issued for PCT/US2015/038171 (dated Dec. 8, 2015).

CN Office Action in Chinese Appln. No. 201580045324.X, dated Jan. 16, 2020, 6 pages.

Allanach et al., "Comparing microarray versus RT-PCR assessment of renal allograft biopsies: Similar performance despite different dynamic ranges," American Journal of Transplantation, 2008, 8:1006-1015.

AU Office Action in Australian Appln. No. 2015229270, dated Jul. 9, 2020, 8 pages.

AU Office Action in Australian Appln. No. 2015279542, dated Aug. 28, 2020, 5 pages.

AU Office Action in Australian Appln. No. 2015279542, dated May 11, 2021, 3 pages.

AU Office Action in Australian Appln. No. 2015279621, dated Aug. 28, 2020, 4 pages.

Ben-Dov et al., "MicroRNA sequence profiles of human kidney allografts with or without tubulointerstitial fibrosis," Transplantation, Dec. 15, 2012, 94(11):1086-1094.

BR Office Action in Brazilian Appln. No. 112016030313-0, dated Dec. 10, 2019, 4 pages (English Translation Only).

BR Office Action in Brazilian Appln. No. 112016030360-1, dated Nov. 29, 2019, 5 pages (English Translation Only).

CA Office Action in Canadian Appln. No. 2942384, dated Mar. 11, 2021, 7 pages.

Chapman, "Do protocol transplant biopsies improve kidney transplant outcomes?," Curr Opin Nephrol Hypertens, Nov. 2012, 21:580-586.

Cheung et al., "Natural variation in human gene expression assessed in lymphoblastoid cells," Nature Genetics, Feb. 3, 2003, 33:422-425.

Cho et al., "Pirfenidone: an anti-fibrotic therapy for progressive kidney disease," Expert Opinion on Investigational Drugs, Feb. 2010, 19(2):275-283.

CN Office Action in Chinese Appln. No. 201580024911.0, dated Dec. 1, 2017, 17 pages (with English Translation).

CN Office Action in Chinese Appln. No. 201580045235.5, dated Jan. 16, 2020, 8 pages (English translation).

CN Office Action in Chinese Appln. No. 201811063221.8, dated Jun. 1, 2021, 18 pages (with English Translation).

Cobb et al., "Sepsis gene expression profiling: Murine splenic compared with hepatic responses determined by using complementary DNA microarrays," Crit. Care Med., 2002, 30(12):2711-2721.

Cosio et al., "Predicting subsequent decline in kidney allograft function from early surveillance biopsies," American Journal of Transplantation, Oct. 2005, 5:2464-2472.

Einecke et al., "A molecular classifier for predicting future graft loss in late kidney transplant biopsies," The Journal of Clinical Investigation, 2010, 120:1862-72.

El-Zoghby et al., "Identifying specific causes of kidney allograft loss," American Journal of Transplantation, Mar. 2009, 9:527-35.

EP Extended European Search Report in European Application No. 15761612.9, dated Aug. 2, 2017, 7 pages.

EP Extended European Search Report in European Application No. EP110466HV, dated Feb. 1, 2018, 10 pages.

EP Office Action in European Application No. 15811195.5, dated Jul. 9, 2019, 4 pages.

Furness et al., "International variation in histologic grading is large, and persistent feedback does not improve reproducibility," Am J Surg Pathol, Jun. 2003, 27:805-810.

Gorantla et al., "Immunosuppressive agents in transplantation: mechanisms of action and current anti-rejection strategies," Microsurgery, Feb. 2000, 20:420-429.

Hai et al., "Changes of early response gene expression profile of peripheral lymphocytes in human renal allograft recipients," Journal of Clinical Rehabilitative Tissue Engineering Research, 2009, 13(5):841-844 (with English Abstract).

Hayry et al., "Protocol core needle biopsy and histological chronic allograft damage index as surrogate endpoint for Long-Term graft survival," Transplant Proc, Jan.-Feb. 2004, 36:89-91.

Hoshikawa et al., "Hypoxia induces different genes in the lungs of rats compared with mice," Physiol Genomics, Dec. 3, 2002, 12:209-219.

Irizarry et al., "Summaries of Affymetrix GeneChip probe level data," Nucleic Acids Research, 2003, 31:e15.

Isoniemi et al., "Histological chronic allograft damage index accurately predicts chronic renal allograft rejection," Transplantation, Dec. 1994, 58:1195-1198.

Johnson and Li, "Adjusting batch effects in microarray expression data using empirical Bayes methods," Biostatistics, 2007, 8:118-127.

Karczewski et al., "Cytometric analysis of TH1/TH2 cytokines in the urine of patients undergoing kidney transplantation," Annals of Transplantation, 2009, 14(3):25-28.

Kulkarni, Meghana M. "Digital multiplexed gene expression analysis using the NanoString nCounter system," Current Protocols in Molecular Biology, Apr. 1, 2011: 25B-10.1-25B10.17.

Kurtkoti et al., "The utility of 1- and 3-month protocol biopsies on renal allograft function: a randomized controlled study," American Journal of Transplantation, Feb. 2008, 8:317-23.

Li et al., "Fast and accurate short read alignment with Burrows-Wheeler transform," Bioinformatics, 2009, 25(14):1754-1760.

Malkov et al. "Multiplexed measurements of gene signatures in different analytes using the Nanostring nCounter Assay System" BMC Research Notes, May 9, 2009 (May 9, 2009), vol. 2, pp. 1-9. entire document.

Maluf et al., "The urine microRNA profile may help monitor post-transplant renal graft function," Kidney International, Jan. 1, 2014, 85(2):439-449.

Mannon et al., "Inflammation in areas of tubular atrophy in kidney allograft biopsies: a potent predictor of allograft failure," American Journal of Transplantation, 2010; 10:2066-73.

Meier-Kriesche et al., "Lack of improvement in renal allograft survival despite a marked decrease in acute rejection rates over the most recent era," American Journal of Transplantation, Jan. 2004, 4:378-83.

(56) References Cited

OTHER PUBLICATIONS

Mengel et al., "Banff 2011 Meeting report: new concepts in antibody-mediated rejection," American Journal of Transplantation, 2012, 12:563-570.
Menon et al., "Moving biomarkers toward clinical implementation in kidney transplantation," Journal of the American Society of Nephrology, 2017, 28:735-747.
Miller et al., "A new method for stranded whole transcriptome RNA-seq," Methods, 2013, 63(2):126-134.
Morgun et al., "Molecular profiling improves diagnoses of rejection and infection in transplanted organs," Circulation Research, 2006, 98(12):e74-e83.
Mueller et al., "Microarray analysis of rejection in human kidney transplants using pathogenesis-based transcript sets," American Journal of Transplantation, 2007, 7(2):2712-2722.
Naesens et al., "Progressive histological damage in renal allografts is associated with expression of innate and adaptive immunity genes," Kidney International, Dec. 2011, 80:1364-76.
Nankivell et al., "Effect of histological damage on long-term kidney transplant outcome," Transplantation, Feb. 2001, 71:515-523.
Nankivell et al., "The natural history of chronic allograft nephropathy," N Engl J Med, 2003, 349:2326-33.
Nguyen et al. "Molecular Mechanisms Involved in Calcineurin Inhibitor Nephrotoxicity in Kidney Allograft Transplants," Master's Thesis, Virginia Commonwealth University, Aug. 8, 2011 (Aug. 8, 2011), pp. 1-74. Retrieved from the Internet< ttp://scholarscompass.vcu.edu/etd/2545/> on May 7, 2015 (May 7, 2015). entire document.
Omran et al., "MicroRNAs: New Insights into Chronic Childhood Diseases," BioMed Research International, Jul. 7, 2013, 2013:13 pages.
Park et al., "Fibrosis with inflammation at one year predicts transplant functional decline," J Am Soc Nephrol, 2010, 21:1987-97.
PCT International Preliminary Report on Patentability in International Application No. PCT/US2015/038147, dated Dec. 27, 2016, 10 pages.
PCT International Preliminary Report on Patentability in International Appln. No. PCT/US2019/027618, dated Oct. 20, 2020, 9 pages.
PCT International Search Report and Written Opinion in International Appln. No. PCT/US2015/020291, dated Jun. 11, 2015, 15 pages.
PCT International Search Report and Written Opinion in International Appln. No. PCT/US2019/027618, dated Jul. 10, 2019, 12 pages.
PCT International Search Report and Written Opinion in International Appln. No. PCT/US2015/038147, dated Oct. 23, 2015, 11 pages.
Ritchie et al., "*limma* powers differential expression analyses for RNA-sequencing and microarray studies," Nucleic Acids Research, 2015, 43(7):e47.
Rush et al., "Beneficial effects of treatment of early subclinical rejection: a randomized study," J Am Soc Nephrol, 1998, 9:2129-34.
Rush et al., "Lack of benefit of early protocol biopsies in renal transplant patients receiving TAC and MMF: a randomized study," American Journal of Transplantation, Nov. 2007, 7:2538-45.
Scherer et al., "Transcriptome changes in renal allograft protocol biopsies at 3 months precede the onset of interstitial fibrosis/tubular atrophy (IF/TA) at 6 months," Nephrol Dial Transplant, 2009, 24:2567-75.
Schwarz et al., "Safety and adequacy of renal transplant protocol biopsies," American Journal of Transplantation, Aug. 2005, 5:1992-6.
Seron et al., "Early protocol renal allograft biopsies and graft outcome," Kidney Int, Jan. 1997, 51:310-316.
Seron et al., "Reliability of chronic allograft nephropathy diagnosis in sequential protocol biopsies," Kidney Int, 2002, 61:727-33.
Shishido et al., "The impact of repeated subclinical acute rejection on the progression of chronic allograft nephropathy," J Am Soc Nephrol, 2003, 14:1046-52.
Solez et al., "Banff 07 classification of renal allograft pathology: updates and future directions," American Journal of Transplantation, 2008, 8:753-760.
Spector et al., "Development and Validation of a MicroRNA-Based Diagnostic Assay for Classification of Renal Cell Carcinomas," Molecular Oncology, Mar. 26, 2013, 7:732-738.
Spivey et al., "Gene expression profiling in acute allograft rejection: challenging the immunologic constant of rejection hypothesis," Journal of Translational Medicine, 2011, 9:1-22.
Stegall et al., "The histology of solitary renal allografts at 1 and 5 years after transplantation," American Journal of Transplantation, Apr. 2011, 11:698-707.
Subramanian et al., "Gene set enrichment analysis: a knowledge-based approach for interpreting genome-wide expression profiles," PNAS, Oct. 2005, 102:15545-50.
Wolfe et al., "Trends in organ donation and transplantation in the United States, 1999-2008," American Journal of Transplantation, Apr. 2010, 10:961-72.
Yilmaz et al, "Clinical predictors of renal allograft histopathology: a comparative study of single-lesion histology versus a composite, quantitative scoring system," Transplantation, Mar. 2007, 83:671-676.
Yilmaz et al., "Protocol core needle biopsy and histologic Chronic Allograft Damage Index (CADI) as surrogate end point for long-term graft survival in multicenter studies," Journal of the American Society of Nephrology, 2003, 14:773-779.
Zhang et al., "Pretransplant transcriptomic signature in peripheral blood predicts early acute rejection," JCI Insight. 2019, 4(11):e127543.
EP Partial Search Report in European Application No. 19789535.2, dated Dec. 6, 2021, 17 pages.
Gökmen-Polar et al., "Elevated protein kinase C β11 is an early promotive event in colon carcinogenesis," Cancer Research, 2001, 61(4):1375-1381.
Haynes et al., "Proteome analysis: Biological assay or data archive?," Electrophoresis, 1998, 19(11):1862-1871.
NCBI [Online], "NCBI GEO Platform GPL570—Affymetrix Human Genome U133 Plus 2.0 Array," Nov. 7, 2003, [Retrieved on Jun. 10, 2022], retrieved from URL<ncbi.nlm.nih.gov/geo/query/acc.cgi?acc=GPL570>, 4 pages.
Tuttle et al., "Placental lactogen is expressed but is not translated into protein in breast cancer," PLOS ONE, 2014, 9(1):e87325.
CA Office Action in Canadian Appln. No. 2942384, dated Jan. 14, 2022, 5 pages.
U.S. Appl. No. 15/125,009, filed Sep. 9, 2016, Barbara Murphy.
U.S. Appl. No. 17/164,607, filed Feb. 1, 2021, Barbara Murphy.
U.S. Appl. No. 15/320,208, filed Dec. 19, 2016, Barbara Murphy.
U.S. Appl. No. 16/424,014, filed May 28, 2019, Barbara Murphy.
U.S. Appl. No. 17/046,692, filed Oct. 9, 2020, Barbara Murphy.
Alakulppi et al., "Diagnosis of Acute Renal Allograft Rejection by Analyzing Whole Blood mRNA Expression of Lymphocyte Marker Molecules," Transplantation, Mar. 2007, 83(6):791-798.
Bontadini, "HLA techniques: Typing and antibody detection in the laboratory of immunogenetics," Methods, Apr. 2012, 56(4):471-576.
BR Office Action in Brazilian Appln. No. 112016020987-7, dated Oct. 8, 2019, 5 pages (English Translation Only).
CA Office Action in Canadian Appln. No. 2953368, dated May 4, 2021, 4 pages.
CA Office Action in Canadian Appln. No. 2953369, dated May 3, 2021, 4 pages.
CA Office Action in Canadian Appln. No. 2953369, dated Apr. 6, 2022, 3 pages.
Chen et al., "Changes of early response gene expression profile of peripheral lymphocytes in human renal allograft recipients," Journal of Clinical Rehabilitative Tissue Engineering Research, Jan. 29, 2009, 13(5):841-844 (with English abstract).
CN Office Action in Chinese Appln. No. 201580045324.X, dated Dec. 24, 2020, 10 pages (with English translation).
EP Extended European Search Report in European Application No. 19789535.2, dated Mar. 10, 2022, 16 pages.

(56) References Cited

OTHER PUBLICATIONS

EP Office Action in European Application No. 15812651.6, dated Oct. 10, 2019, 5 pages.
Hurvich et al., "A Corrected Akaike Information Criterion for Vector Autoregressive Model Selection," Journal of Time Series Analysis, 2008, 14:271-279.
Ihaka, "R: A Language for Data Analysis and Graphics," Journal of Computational and Graphical Statistics, Sep. 1996, 5(3):299-314.
Li et al., "The Sequence Alignment/Map format and SAMtools," Bioinformatics. Aug. 2009; 25(16):2078-2079.
Mata et al., "A Hexameric Phosphorothioate Oligonucleotide Telomerase Inhibitor Arrests Growth of Burkitt's Lymphoma Cells in Vitro and in Vivo," Toxicology Applied Pharmacology, May 1997, 144:189-197.
Mootha et al., "PGC-1alpha-responsive genes involved in oxidative phosphorylation are coordinately downregulated in human diabetes," Nat Genet, 2003, 34:267-273.
Samstag et al., "Synthesis and Properties of New Antisense Oligodeoxynucleotides Containing Benzylphosphonate Linkages," Antisense Nucleic Acid Drug Development, 1996, 6:153-156.
Strauss-Soukup et al., "Effects of Neutralization Pattern and Stereochemistry on DNA Bending by Methylphosphonate Substitutions,'" Biochemistry, Jul. 1997, 36:8692-8698.
Tibshirani et al., "Regression Shrinkage and Selection via the Lasso," Journal of the Royal Statistical Society Series B, 1996, 58:267-288.
Tran et al., "Inferring causal genomic alterations in breast cancer using gene expression data," BMC Syst Biol, Aug. 2011, 5:121.
Trapnell et al., "Differential gene and transcript expression analysis of RNA-seq experiments with TopHat and Cufflinks," Nat Protoc, Mar. 2012, 7:562-578.
Vahed et al., "Diagnosis of Interstitial Fibrosis and Tubular Atrophy in Kidney Allograft: Implementation of MicroRNAs ", Iranian Journal of Kidney Diseases, Jan. 2014, 8(1):4-12.
Zhu et al., "Integrating large-scale functional genomic data to dissect the complexity of yeast regulatory networks," Nat Genet, Jul. 2008, 40:854-861.

* cited by examiner

METHOD FOR DIAGNOSING SUBCLINICAL AND CLINICAL ACUTE REJECTION BY ANALYSIS OF PREDICTIVE GENE SETS

CROSS-REFERENCE TO RELATED APPLICATIONS

This application claims the benefit of U.S. Application No. 62/017,784, filed on Jun. 26, 2014, which is incorporated by reference herein in its entirety.

GOVERNMENT CLAUSE

This invention was made with government support under 1U01AI070107-01 awarded by The National Institutes of Health. The government has certain rights in the invention.

TECHNICAL FIELD

This invention relates to methods for diagnosing acute cellular rejection (ACR) of an allograft by analysis of predictive gene sets and kits for practicing these methods. The methods comprise analyzing the blood of kidney allografts recipients by determining the expression level of a gene signature set containing at least 7 preselected genes in order to identify and treat such patients. An altered expression level of one or more genes in the blood of the allograft recipient compared to the same genes in a control indicates the patient is at risk for allograft rejection. The greater the level of alteration, the greater the risk of rejection. A logistic regression fitting model can be applied to normalized expression values (e.g. read counts of genes from next generation sequencing technology) to derive a tatistical model from which a probability score for risk of acute cellular rejection can be calculated for each patient.

BACKGROUND OF THE INVENTION

The existing tests for renal allograft rejection are cumbersome and expensive. Such tests usually require obtaining a biopsy specimen from the patient. Often by the time rejection is recognized it is too late to do anything. An increase in serum creatinine or an increase of protein in the urine may be warnings of rejection but are not entirely predictive. There has been a need in the field for an improved assay that is easy to conduct, eliminates the need for a biopsy and is more predictive of the risk of renal allograft rejection or fibrosis.

The present expression profile test addresses this need and provides a blood based assay that is easily administered repetitively to transplant patients. Renal transplant patients are examined by their physician very frequently post transplantation—in most instances twice per week for the first month moving to weekly and then every other week getting to monthly after 4 to 5 months, with time intervals between visits gradually increasing thereafter. During this time, the patients' renal function and the immunosuppression levels are monitored. Steroids are tapered to 5 mg by 3 months post-surgery and the tacrolimus (a drug that suppresses the immune system and is used to prevent rejection of transplanted organs) levels are gradually reduced to a steady level by 6-12 months if the post-transplant course has no complications and the patient is not high immunological risk. The gene expression profiles described below can be employed as a standard test to be performed at the time of a clinical visit. A positive test result (i.e. the patient is expressing these genes at an altered level compared to a control) indicates that the patient is at risk of rejecting the transplanted organ, and would be treated by increasing the dose of immunosuppressive drugs and by discontinuing the customary taper of immunosuppressive drugs. Repeat testing (which can be done economically since the assay is preferably a blood based test) will guide the reinitiation of immunosuppression tapering. Thus, for example if 2 subsequent tests were negative the prednisone dose may decrease by 2.5 or 5 mg, or the target level for tacrolimus would be lowered by 0.5 mg/dl. If the profile test is positive in the presence of an increase in creatinine this would indicate a clinical acute rejection as evidenced by renal injury. In this instance, the patient would be treated with either high dose steroids or antilymphocyte agents depending on the overall immunological risk of the individual.

SUMMARY OF THE INVENTION

In one aspect, a method is provided for identifying a kidney allograft recipient at risk of allograft rejection or loss by obtaining a biological specimen from the renal allograft recipient, measuring the expression level of a preselected gene signature set in the specimen, comparing the expression level of the preselected gene signature set in the specimen with the expression level of the preselected gene signature set in a control, determining that the allograft recipient is at increased risk for rejection of the allograft if the expression level of the gene signature set in the specimen is altered compared to the expression level in the control.

In another aspect, a method is provided for identifying a kidney allograft recipient at risk of allograft rejection or loss by obtaining a biological specimen from the renal allograft recipient, measuring the expression level of a preselected gene signature set in the specimen, comparing the expression level of the preselected gene signature set in the specimen with the expression level of the preselected gene signature set in a control, determining that the allograft recipient is at increased risk for rejection of the allograft if the expression level of one or more genes in the gene signature set in the specimen is altered compared to the expression level of one or more genes in the gene signature set in the control.

In another aspect, a method is provided for treating a kidney allograft recipient at risk of allograft rejection or loss by obtaining a biological specimen from the renal allograft recipient, measuring the expression level of a preselected gene signature set in the specimen, comparing the expression level of the preselected gene signature set in the specimen with the expression level of the preselected gene signature set in a control sample, determining that the allograft recipient is at increased risk for rejection of the allograft if the expression level of the gene signature set in the specimen is altered compared to the expression level of the preselected gene signature set in the control and treating a recipient determined to be at risk of rejection.

In another aspect, a method is provided for treating a kidney allograft recipient at risk of allograft rejection or loss by obtaining a biological specimen from the renal allograft recipient, measuring the expression level of a preselected gene signature set in the specimen, comparing the expression level of the preselected gene signature set in the specimen with the expression level of a control sample, determining that the allograft recipient is at increased risk for rejection of the allograft if the expression level of one or more genes in the gene signature set in the specimen is altered compared to the expression level of one or more genes in the gene signature set in the control and treating a recipient determined to be at risk of rejection In another embodiment, a method is provided for treating a kidney allograft recipient by obtaining a biological specimen from the allograft recipient, measuring the expression level of a selected gene set in the specimen, comparing the expression level of the gene set in the specimen with the expression level of a control patient, determining that the recipient is at risk for rejection of the allograft if the expression level of the gene set in the specimen is altered compared to the expression level of the gene set in the control, and treating a recipient determined to be at risk of rejection.

In another embodiment, a method is provided for treating a kidney allograft recipient by obtaining a biological specimen from the allograft recipient, measuring the expression level of a selected gene set in the specimen, comparing the expression level of the gene set in the specimen with the expression level of a control, determining that the recipient is at risk for rejection of the allograft if the expression level of one or more members of the gene set in the specimen is altered compared to the expression level of one or more members of the gene signature set in the control, and treating a recipient determined to be at risk of rejection.

Another embodiment provides a method for treating a kidney allograft recipient by obtaining a biological specimen from the allograft recipient, measuring the expression level of a selected gene set in the specimen, comparing the expression level of the gene set in the specimen with the expression level of a control, determining that the patient is at risk of rejection of the allograft if the expression level of the gene set in the specimen is altered relative to the expression level of the gene set in the control, and treating the recipient determined to be at risk of rejection by administering immunosuppressive drugs to the recipient or by administering high dose steroids or antilymphocyte agents.

Another embodiment provides a method for treating a kidney allograft recipient by obtaining a biological specimen from the allograft recipient, measuring the expression level of a selected gene set in the specimen, comparing the expression level of the gene set in the specimen with the expression level of the gene set in a control, determining that the patient is at risk of rejection of the allograft if the expression level of one or more genes of the gene set in the specimen is altered relative to the expression level of one or more members of the gene set in the control, and treating the recipient determined to be at risk of rejection by administering immunosuppressive drugs to the recipient or by administering high dose steroids or antilymphocyte agents.

In another aspect a kit for use in determining if an allograft recipient is at risk of ACR is provided. The kit comprises an assay for a preselected gene signature set, primers for a preselected gene signature set, buffers and positive and negative controls and instructions for use.

In one aspect, a sequencing panel is provided comprising at least 7 genes from among the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1

In another aspect, a sequencing panel is provided comprising the genes ANXA5, TSC22D1, AP1M1, CLK1, EFTUD2, SENP6, and SENP7

In another aspect, a sequencing panel is provided comprising the genes TSC22D1, ANKA5, EFTUD2, AP1M1, MAP1A, C1GALT1C1, SENP6, CLK1 and SENP7.

In another aspect, a sequencing panel is provided comprising the genes CCDC82, F13A1, TUBB1, TSC22D1, SENP6, ANXA5, EFTUD2, SENP7, AP1M1, CLK1, and C1GALT1C1.

In another aspect, a sequencing panel is provided comprising the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1.

Yet another aspect is an assay kit for identifying renal allograft recipients suffering from subclinical and clinical acute rejection and at risk for allograft loss comprising in one or more separate containers: an assay for a gene signature set comprising at least the genes ANXA5, TSC22D1, AP1M1, CLK1, EFTUD2, SENP6, and SENP7, buffers, positive and negative controls and instructions for use.

Yet another aspect is an assay kit for identifying renal allograft recipients suffering from subclinical and clinical acute rejection and at risk for allograft loss comprising in one or more separate containers: an assay for a gene signature set comprising at least the genes TSC22D1, ANKA5, EFTUD2, AP1M1, MAP1A, C1GALT1C1, SENP6, CLK1 and SENP7, buffers, positive and negative controls and instructions for use.

Yet another aspect is an assay kit for identifying renal allograft recipients suffering from subclinical and clinical acute rejection and at risk for allograft loss comprising in one or more separate containers: an assay for a gene signature set comprising at least the genes CCDC82, F13A1, TUBB1, TSC22D1, SENP6, ANXA5, EFTUD2, SENP7, AP1M1, CLK1, and C1GALT1C1, buffers, positive and negative controls and instructions for use.

Another aspect is an assay kit for identifying renal allograft recipients suffering from subclinical and clinical acute rejection and at risk for allograft loss comprising in one or more separate containers: an assay for a gene signature set comprising at least the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1, buffers, positive and negative controls and instructions for use.

Another aspect of the invention is an assay kit for identifying renal allograft recipients suffering from subclinical and clinical acute rejection and at risk for allograft loss comprising in one or more separate containers: an assay for a gene signature set comprising genes selected from the group consisting of SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1, buffers, positive and negative controls and instructions for use.

A further aspect-provides a method for identifying kidney allograft recipients suffering from subclinical and clinical acute rejection and at risk for graft loss comprising the steps of providing a blood specimen from a renal allograft recipient, isolating mRNA from the blood specimen, synthesizing cDNA from the mRNA, and measuring the expression levels of a gene panel comprising a preselected gene signature set with MiSEQ sequence system (Illumina, Inc. San Diego Calif.), Nanostring (nCounter® miRNA Expression Assay-Nanostring Technologies, Inc. Seattle Wash.) or qPCR. The results of the gene set analysis are compared to a control. The gene expression result can be used to predict the onset of an allograft rejection response, to diagnose an allograft rejection response, and/or to characterize an allograft rejection response in a transplant patient. If the patient is expressing the gene signature set at an altered level relative to the expression level in the control, the patient is at risk for rejection. The greater the patients expression level of the signature gene set is altered compared to the control, the greater the risk of rejection.

In another aspect, the results of the assay are applied to a penalized logistic regression fitting model (log (p(x))/(1−p(x))=β*0+β*1g1+β*igi+ . . . +β*ngn (where (p(x) is the probability of ACR, β*i is penalized coefficiency and gi is the read count of gene i) that can be used to compute a probability score for acute rejection for each patient.

In another aspect the invention provides a method for assessing the likelihood of renal graft rejection in a patient by determining the level of expression of a preselected gene set containing at least the genes ANXA5, TSC22D1, AP1M1, CLK1, EFTUD2, SENP6, and SENP7, in a sample from the patient and comparing the expression level of the preselected gene set genes in the sample with the expression level of the preselected gene set genes in a control to assess the likelihood of renal graft rejection in the patient.

In another aspect the invention provides a method for assessing the likelihood of renal graft rejection in a patient by determining the level of expression of a preselected gene set containing at least the genes TSC22D1, ANKA5, EFTUD2, AP1M1, MAP1A, C1GALT1C1, SENP6, CLK1 and SENP7 in a sample from the patient and comparing the expression level of the preselected gene set genes in the sample with the expression level of the preselected gene set genes in a control to assess the likelihood of renal graft rejection in the patient.

In another aspect the invention provides a method for assessing the likelihood of renal graft rejection in a patient by determining the level of expression of a preselected gene set containing at least the genes CCDC82, F13A1, TUBB1, TSC22D1, SENP6, ANXA5, EFTUD2, SENP7, AP1M1, CLK1, and C1GALT1C1 in a sample from the patient and comparing the expression level of the preselected gene set genes in the sample with the expression level of the gene set genes in a control to assess the likelihood of renal graft rejection in the patient.

In another aspect the invention provides a method for assessing the likelihood of renal graft rejection in a patient by determining the level of expression of a preselected gene set containing at least the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1 in a sample from the patient and comparing the expression level of the preselected gene set genes in the sample with the expression level of the preselected gene set genes in a control to assess the likelihood of renal graft rejection in the patient.

In another aspect the invention provides a method of determining whether a patient that has received an allograft is undergoing an acute rejection of the allograft by evaluating the expression level of a gene set comprising at least the genes ANXA5, TSC22D1, AP1M1, CLK1, EFTUD2, SENP6, and SENP7 from a sample from the patient who has received the allograft and comparing the gene set expression level in the sample with the expression level of the gene set genes in a control to assess the likelihood of renal graft rejection in the patient.

In another aspect the invention provides a method of determining whether a patient that has received an allograft is undergoing an acute rejection of the allograft by evaluating the expression level of a gene set comprising at least the genes TSC22D1, ANKA5, EFTUD2, AP1M1, MAP1A, C1GALT1C1, SENP6, CLK1 and SENP7 from a sample from the patient who has received the allograft and comparing the gene set expression level in the sample with the expression level of the gene set genes in a control to assess the likelihood of renal graft rejection in the patient.

In another aspect the invention provides a method of determining whether a patient that has received an allograft is undergoing an acute rejection of the allograft by evaluating the expression level of a gene set comprising at least the genes CCDC82, F13A1, TUBB1, TSC22D1, SENP6, ANXA5, EFTUD2, SENP7, AP1M1, CLK1, and C1GALT1C1 from a sample from the patient who has received the allograft and comparing the gene set expression level in the sample with the expression level of the gene set genes in a control to assess the likelihood of renal graft rejection in the patient.

In another aspect the invention provides a method for assessing the likelihood of renal graft rejection in a patient by determining the level of expression of a preselected gene set containing at least the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1 in a sample from the patient and comparing the expression level of the preselected gene set genes in the sample with the expression level of the gene set genes in a control to assess the likelihood of renal graft rejection in the patient.

In another aspect the invention provides a method of determining whether a patient that has received an allograft is undergoing an acute rejection of the allograft by evaluating the expression level of a gene set comprising at least the genes TSC22D1, ANKA5, EFTUD2, AP1M1, C1GALT1C1, SENP6, CLK1 and SENP7 from a sample from the patient who has received the allograft.

In another aspect the invention provides a method of determining whether a patient that has received an allograft is undergoing an acute rejection of the allograft by evaluating the expression level of an eleven member gene set comprising at least the genes CCDC82, F13A1, TUBB1, TSC22D1, SENP6, ANXA5, EFTUD2, SENP7, AP1M1, CLK1, and C1GALT1C1 from a sample from the patient who has received the allograft In another aspect the invention provides a method of determining whether a patient that has received an allograft is undergoing an acute rejection of the allograft by evaluating the expression level of a 17 member gene set comprising at least the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1 from a sample from the patient who has received the allograft.

In another aspect the invention provides a kit for determining whether a patient that has received an allograft is undergoing an acute rejection of the allograft comprising in one or more containers primer pairs for the preselected gene set, positive and negative controls, buffers and instructions for use.

In another aspect the invention provides a kit for determining whether a patient that has received an allograft is undergoing an acute rejection of the allograft comprising in one or more containers primer pairs for a 17 member gene set, positive and negative controls, buffers and instructions for use.

In another aspect the invention provides a kit for determining whether a patient that has received an allograft is undergoing an acute rejection of the allograft comprising in one or more containers primer pairs for an 11 member gene set, positive and negative controls, buffers and instructions for use.

In another aspect the invention provides a kit for determining whether a patient that has received an allograft is undergoing an acute rejection of the allograft comprising in one or more containers primer pairs for a 9 member gene set, positive and negative controls, buffers and instructions for use.

In another aspect the invention provides a kit for determining whether a patient that has received an allograft is undergoing an acute rejection of the allograft comprising in one or more containers primer pairs for a 7 member gene set, positive and negative controls, buffers and instructions for use.

In another aspect the invention provides a method for selecting a renal allograft recipient for treatment to reduce the risk of renal allograft rejection which comprises
(a) providing a blood specimen from the renal allograft recipient;
(b) determining the expression levels of a preselected gene set in the specimen;
(c) comparing the expression levels of the preselected gene set genes in the specimen with the expression levels of the preselected gene set genes in a control, and
(d) selecting the recipient for treatment for allograft rejection if the expression level of one or more genes in the gene set in the specimen is altered compared to the expression level of one or more of the gene set genes in the control In another aspect the invention provides a method of selecting a renal allograft patient for treatment to reduce the risk of renal allograft rejection or allograft loss which comprises comparing the expression level of a preselected gene set obtained from the patient with the expression level of the preselected gene set in a control sample obtained from an allograft recipient that did not suffer allograft rejection, and selecting the patient for treatment for allograft rejection or loss if the expression level of one or more genes in the preselected gene set from the patient is altered compared to the expression level of one or more of the preselected gene set genes in the control.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Definitions

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

As used herein "ACR" means acute cellular rejection.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year The terms "decrease", "decreased", "reduced", "reduction" or "down-regulated" are all used herein generally to mean a decrease by a statistically significant amount. However, for avoidance of doubt, "reduced", "reduction", "down-regulated" "decreased" or "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a reference level.

The terms "increased", "increase" or "up-regulated" are all used herein to generally mean an increase by a statistically significant amount; for the avoidance of any doubt, the terms "increased" or "increase" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a reference level.

As used herein, "determining the level of expression," "determining the expression level" or "detecting the level of express", as in, for example, "determining the expression level of a gene refers to quantifying the amount of mRNA present in a sample. Detecting expression of the specific mRNAs, can be achieved using any method known in the art or described herein. Typically, mRNA detection methods involve sequence specific detection, such as by RT-PCR. mRNA-specific primers and probes can be designed using nucleic acid sequences, which are known in the art.

Throughout the application and in the appended claims, it should be understood and is intended to be understood that use of the terms "drug", "medication", "agent" and "therapeutic agent" are interchangeable expressions defining the same or similar entities. A "drug" refers generally to a chemical compound, small molecule, or other biologic composition, such as an antisense compound, antibody, protease inhibitor, hormone, chemokine or cytokine, capable of inducing a desired therapeutic or prophylactic effect when properly administered to a subject.

As used herein, "treating" or "treatment" of a state, disorder or condition includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition (e.g., fibrosis of a renal allograft and/or allograft loss); and/or (2) inhibiting the state, disorder or condition, i.e., arresting, reducing or delaying the development of the disease or a relapse thereof (in case of maintenance treatment) or at least one clinical or sub-clinical symptom thereof; and/or (3) relieving the disease, i.e., causing regression of the state, disorder or condition or at least one of its clinical or sub-clinical symptoms; and/or (4) causing a decrease in the severity of one or more symptoms of the disease. The benefit to a subject to be treated is either statistically significant or at least perceptible to the patient or to the physician.

As used herein, the term "inhibiting" of disease or condition (e.g. ACR and/or allograft loss) means for example, to stop the development of one or more symptoms of a disease in a subject before they occur or are detectable, e.g., by the patient or the patient's doctor. Preferably, the disease or condition does not develop at all, i.e., no symptoms of the disease are detectable. However, it can also result in delaying or slowing of the development of one or more symptoms of the disease.

As used herein, a "altered" level of expression of a mRNA compared to reference level or control level is an at least 0.5-fold (e.g., at least: 1-2-; 3-; 4-; 5-; 6-; 7-; 8-; 9-; 10-; 15-; 20-; 30-; 40-; 50-; 75-; 100-; 200-; 500-; 1,000-; 2000-; 5,000-; or 10,000-fold) altered level of expression of the mRNA. It is understood that the alteration can be an increase or a decrease. Alternatively, altered expression level is defined as an increase in the acute rejection probability score using parameters in the logistic regression model established from a training patient group, comparing the probability score to the cutoff derived from the training set.

"Control" is defined as a sample obtained from a patient that received an allograft transplant that is not suffering from acute cellular rejection.

It has now been determined that enhanced transcription of a preselected set of genes can be used to predict the likelihood that a renal allograft recipient will reject a transplanted kidney before the patient manifests any overt symptoms. The assay can also be employed to diagnose whether a kidney transplant patient is experiencing acute rejection. Over expression of the gene sets can be used to identify patients at risk for acute rejection.

If the patient is expressing the preselected genes at an altered level relative to control, the patient is at risk for rejection. The greater the alteration in the expression level of the preselected genes compared to the control, the greater the risk of rejection. The information obtained with the assay can also be applied to a penalized logistic regression fitting model (log $(p(x))/(1-p(x))=\beta*0+\beta*1g1+\beta*igi+ \ldots +\beta*9g9$ (where $p(x)$ is the probability of ACR, $\beta*i$ is penalized coefficiency and gi is the read count of gene i), that can be used to compute a probability score for acute rejection for each patient. In one embodiment, a higher score above indicates that the patient is at high risk of rejecting the transplanted organ.

Currently, the diagnosis of acute rejection requires a renal allograft biopsy triggered by an elevation of creatinine in the presence of renal injury. The collection and assaying of patient biopsy samples is time consuming and expensive. The present assay technique is a biological tissue assay, preferably a blood based assay that avoids the need for biopsy specimens. The assay can be used to predict the likelihood that a renal allograft recipient will reject a transplanted kidney before the patient manifests any overt symptoms. The assay can also be employed to diagnose whether a kidney transplant patient is experiencing acute rejection. The assay is inexpensive, highly accurate, reproducible and non-invasive.

Peripheral blood signatures using gene signature sets comprising at least 7 and up to 17 preselected genes have been identified. These preselected gene sets can be used to accurately diagnose subclinical rejection of kidney allografts and identify kidney allografts at risk for subsequent histological and functional decline as well as the risk of graft rejection.

The gene signature sets useful in practicing the methods disclosed herein are selected from the following genes: SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1.

The seven gene peripheral blood signature set of the present invention is: ANXA5, TSC22D1, AP1M1, CLK1, EFTUD2, SENP6, and SENP7.

The nine gene peripheral blood signature of the present invention is: TSC22D1, ANKA5, EFTUD2, AP1M1, MAP1A, C1GALT1C1, SENP6, CLK1 and SENP7.

The 11-gene peripheral blood signature of the present invention is: CCDC82, F13A1, TUBB1, TSC22D1, SENP6, ANXA5, EFTUD2, SENP7, AP1M1, CLK1, and C1GALT1C1.

The 17-gene peripheral blood signature of the present invention is: SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1.

Each of these blood signature sets can be used to practice the present invention. However, the 11-gene blood signature set is a preferred embodiment.

The present invention provides a method for identifying kidney allograft recipients suffering from subclinical and clinical acute rejection and at risk for graft loss comprising the steps of providing a blood specimen from a renal allograft recipient, isolating mRNA from the blood specimen, synthesizing cDNA from the mRNA, and measuring the expression levels of a gene panel comprising a selected gene signature set with MiSEQ sequence system (Illumina, Inc. San Diego Calif.), Nanostring (nCounter® miRNA Expression Assay-Nanostring Technologies, Inc. Seattle Wash.) or qPCR. The results of the gene set analysis are compared to a control. The gene expression result can be used to predict the onset of an allograft rejection response, to diagnose an allograft rejection response, and/or to characterize an allograft rejection response in a transplant patient. If the patient is expressing the gene signature set at an altered level relative to the expression level of the gene signature set genes in the control, the patient is at risk for rejection. The greater the patient's expression level is altered compared to the control, the greater the risk of rejection.

In one aspect, a method is provided for treating a kidney allograft recipient by obtaining a biological specimen from the renal allograft recipient, measuring the expression level of a preselected gene signature set in the specimen, comparing the expression level of the preselected gene signature set in the specimen with the expression level of the gene signature genes a control sample, and determining that the allograft recipient is at increased risk for acute T-cell mediated rejection of the allograft if the expression level of the gene signature set in the specimen is altered relative the expression level in the gene signature set in the control.

In another embodiment, a method is provided for treating a kidney allograft recipient by obtaining a biological specimen from the allograft recipient, measuring the expression level of a selected gene set in the specimen, comparing the expression level of the gene set in the specimen with the expression level of a control patient, determining that the recipient is at risk for rejection of the allograft if the expression level of the gene set in the specimen is altered relative to the expression level of the gene set in the control, and treating a patient determined to be at risk of rejection to prevent rejection.

Another embodiment provides a method for treating a kidney allograft recipient by obtaining a biological specimen from the allograft recipient, measuring the expression level of a preselected gene set in the specimen, comparing the expression level of the gene set in the specimen with the expression level of a control, determining that the patient is at risk of rejection if the expression level of the gene set in the specimen is altered relative to the expression level of the gene set in the control, and treating the recipient determined to be at risk of rejection by administering immunosuppressive drugs to the recipient or by administering high dose steroids or antilymphocyte agents In yet another embodiment, an assay kit for identifying renal allograft recipients suffering from subclinical and clinical acute rejection and at risk for allograft loss is provided comprising in one or more separate containers: an assay for a gene signature set comprising at least the genes ANXA5, TSC22D1, AP1M1, CLK1, EFTUD2, SENP6, and SENP7, buffers, positive and negative controls and instructions for use.

In yet another embodiment, an assay kit for identifying renal allograft recipients suffering from subclinical and clinical acute rejection and at risk for allograft loss is provided comprising in one or more separate containers: an assay for a gene signature set comprising at least the genes TSC22D1, ANKA5, EFTUD2, AP1M1, MAP1A, C1GALT1C1, SENP6, CLK1 and SENP7, buffers, positive and negative controls and instructions for use.

Yet another aspect is an assay kit for identifying renal allograft recipients suffering from subclinical and clinical acute rejection and at risk for allograft loss comprising in one or more separate containers: an assay for a gene signature set comprising at least the genes CCDC82, F13A1, TUBB1, TSC22D1, ANXA5, EFTUD2, SENP7, AP1M1, CLK1, and C1GALT1C1, buffers, positive and negative controls and instructions for use.

Yet another aspect is an assay kit for identifying renal allograft recipients suffering from subclinical and clinical acute rejection and at risk for allograft loss comprising in one or more separate containers: an assay for a gene signature set comprising at least the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1, buffers, positive and negative controls and instructions for use.

In a further embodiment, the present invention provides a method for identifying kidney allograft recipients suffering from subclinical and clinical acute rejection and at risk for graft loss comprising the steps of providing a blood specimen from a renal allograft recipient, isolating mRNA from the blood specimen, synthesizing cDNA from the mRNA, and measuring the expression levels of a gene panel comprising a selected nine gene signature set with MiSEQ sequence system (Illumina, Inc. San Diego Calif.), Nanostring (nCounter® miRNA Expression Assay-Nanostring Technologies, Inc. Seattle Wash.) or qPCR. The results of the gene set analysis are compared to the expression level of the signature set genes in a control. The gene expression result can be used to predict the onset of an allograft rejection response, to diagnose an allograft rejection response, and/or to characterize an allograft rejection response in a transplant patient. If the patient is expressing the gene signature set at an altered level relative to the control, the patient is at risk for reject of the signature set genes ion. The greater the alteration (increase and/or decrease) in the patient's expression level of the gene signature genes compared to the control, the greater the risk of rejection.

In another embodiment, the results of the assay are applied to a penalized logistic regression fitting model (log $(p(x)/(1-p(x))=\beta^*0+\beta^*1g1+\beta^*igi+ \ldots +\beta^*ngn$ (where $p(x)$ is the probability of ACR, $\beta^*i$ is penalized coefficiency and gi is the read count of gene i) that can be used to compute a probability score for acute rejection for each patient. If the probability score of the patient is higher than the probability score of the control then the patient is at risk for acute cellular rejection.

In another embodiment the invention provides a method of determining whether a patient that has received an allograft is undergoing an acute rejection of the allograft by evaluating the expression level of a 17 member gene set comprising at least the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1 from a sample from the patient who has received the allograft.

In some methods herein, it is desirable to detect and quantify mRNAs present in a sample. Detection and quantification of RNA expression can be achieved by any one of a number of methods well known in the art. Using the known sequences for RNA family members, specific probes and primers can be designed for use in the detection methods described below as appropriate.

In some cases, detection and quantification of RNA expression requires isolation of nucleic acid from a sample, such as a cell or tissue sample. Nucleic acids, including RNA and specifically mRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and small interfering RNAs (siRNAs). Extraction procedures such as those using QIAGEN-ALLprep kit are also contemplated.

In some embodiments, use of quantitative RT-PCR is desirable. Quantitative RT-PCR (qRT-PCR) is a modification of polymerase chain reaction used to rapidly measure the quantity of a product of polymerase chain reaction.

qRT-PCR is commonly used for the purpose of determining whether a genetic sequence is present in a sample, and if it is present, the number of copies in the sample. Any method of PCR that can determine the expression of a nucleic acid molecule, including a mRNA, falls within the scope of the present disclosure. There are several variations of the qRT-PCR method known in the art, three of which are described below.

In another embodiment the invention provides a kit for determining whether a patient that has received an allograft is undergoing an acute rejection of the allograft comprising in one or more containers primer pairs for the 17 member gene set, positive and negative controls, buffers and instructions for use.

In a typical embodiment, a clinical lab will obtain the expression value using the patient's sample and send it to the patient's doctor. The doctor will then communicate this value to his web based service provider. The service provider will enter that value in the bioinformatics system which already has the penalized co-efficiency for each gene of the preselected gene set and the cutoff from the logistic regression model from the training set. The bioinformatics system will use this information to calculate the probability score for the patient. The calculated score will reflect the patient's ACR status.

The overall procedure of application of the gene signature in ACR diagnosis is described below using the nine-gene signature as a non-limiting example.

1) Selecting training group: A group of kidney transplant patients with balanced ACR and noACR (control) cases (total number N=~100) will be carefully selected. The training group will have well-characterized demographics and clinical indications which have been reviewed by at least two pathologists.
2) Measuring expression of 9 genes: Expression levels of 9 genes from the blood sample post-transplant of each patient in the training group can be measured using any technique, and preferably by MiSEQ, RT-PCR or Nanostring technology. Use of these techniques is described in Examples 1-3 below.
3) Establishing a regression model and cut off: A penalized logistic regression fitting model using the log istf R package (a statistical package available from r-project.org) will be then applied on expression values of the 9 genes to derive the statistical model from which the $\beta^*$ value will be derived for each gene and the probability score of acute rejection for each patient will be calculated from the following equation:

$$(\log(p(x))/(1-p(x))) = \beta^*0 + \beta^*1 g1 + \beta^* igi + \ldots + \beta^* 9 g9$$

(where $p(x)$ is the probability of ACR, $\beta^*i$ is penalized coefficiency and gi is the read count of gene i)

Based on the probability score, the prediction statistics such as prediction AUC (area under the curve) of ROC (Receive operating characteristic) curve of the true positive rate versus the false positive, sensitivity/specificity, the positive values (PPV) and the negative predictive values (NPV) will be determined. At a given specificity (90%), a probability score cut off will be established which best detects the presence of acute rejection. It is expected that there will be a clear cut off into two groups in that if a patient is in the top group they have a high likelihood of having acute rejection and the test is determined to be positive but if they are in the bottom they have a very low likelihood of having acute rejection and the test is determined to be negative.

The alternative is that patients will be broken in to tertiles based on their probability score determined as above. In this case if the patient is in (1) the top tertile they have a high likelihood of having acute rejection and the test is determined to be positive; (2) the second tertile or intermediate group their risk cannot be accurately determined; and (3) the bottom tertile they have a very low likelihood of having acute rejection and the test is determined to be negative.

The coefficiency ($\beta^*$ value) and the cutoff derived from the training group will be entered and stored into a web-based bioinformatics computer system which can be accessed from clinical lab/doctor office via the internet.

4) Diagnosis of a new case: For a new patient, the expression levels of the 9 gene set will be measured by the same technology used for the training set in the clinical lab. By using a web-based bioinformatics system, the probability score will be calculated by summarizing the expression value (gi) of the 9 genes multiplied by their $\beta^*$ values which are derived from the training set. The probability score will be compared to the cutoff to determine the ACR status. An increase in the probability score in the patient relative to the probability score in a control indicates that the patient is at an increased risk for allograft rejection. A clinical lab will send the testing results to the doctor.

The methods disclosed herein accurately diagnose subclinical and clinical rejection and accurately identify allografts at risk for subsequent histological and functional decline and allograft recipients at risk for graft loss.

When such allografts recipients are identified, the present invention includes methods for treating such patients. The methods include, without limitation, increased administration of immunosuppressive drugs, i.e. a calcineurin inhibitor (CNI), such as cyclosporine or tacrolimus, or a less fibrogenic immunosuppressive drug such as mycophenolate mofetil (MMF) or sirolimus. The main class of immunosuppressants are the calcineurin inhibitors (CNIs), which includes tacrolimus (Prograf® and Advagraf®/Astagraf XL (Astellas Pharma Inc.) and generics of Prograf®) and cyclosporine (Neoral® and Sandimmune® (Novartis AG) and generics). Steroids such as prednisone may also be administered to treat patients at risk for graft loss or functional decline. Antiproliferative agents such as Mycophenolate Mofetil, Mycophenolate Sodium and Azathioprine are also useful in such treatments. Immunosuppression can be achieved with many different drugs, including steroids, targeted antibodies and CNIs like tacrolimus. Of these, tacrolimus is one of the more potent in terms of suppressing the immune system or administration of high dose steroids or antilymphcytic agents depending on the presence or absence of an elevated creatinine. The currently preferred treatment regimen for clinical rejection is either high does steroids or antilymphocytic agents. Another preferred agent is Nulojix® (belatacept, Bristol-Myers Squibb), an infusional biologic agent.

Kits

In certain embodiments, kits are provided for determining a renal allograft recipient's risk for allograft loss.

The kits will contain primers for the 17 member gene signature sea as set forth in Example 5 below (for Nanostring assays), primers for 2 housekeeping genes, beta actin (ACTB) and glyceraldehyde 3-phosphate dehydrogenase (GAPDH), and a control probe, 18S ribosomal RNA (for qPCR assays).

A kit can further contain one or more mRNA extraction reagents and/or reagents for cDNA synthesis. In other embodiments, the kit can comprise, one or more containers into which the biological agents are placed and, preferably, suitably aliquotted. The components of the kits may be packaged either in aqueous media or in lyophilized form. The kits can also comprise one or more pharmaceutically acceptable excipients, diluents, and/or carriers. Non-limiting examples of pharmaceutically acceptable excipients, diluents, and/or carriers include RNAse-free water, distilled water, buffered water, physiological saline, PBS, Ringer's solution, dextrose solution, reaction buffers, labeling buffers, washing buffers, and hybridization buffers.

The kits of the invention can take on a variety of forms. Typically, a kit will include reagents suitable for determining gene set expression levels (e.g., those disclosed herein) in a sample. Optionally, the kits may contain one or more control samples. Also, the kits, in some cases, will include written information (indicia) providing a reference (e.g., predetermined values), wherein a comparison between the gene expression levels in the subject and the reference (predetermined values) is indicative of a clinical status.

In some cases, the kits comprise software useful for comparing gene set expression levels or occurrences with a reference (e.g., a prediction model). Usually the software will be provided in a computer readable format such as a compact disc, but it also may be available for downloading via the internet. However, the kits are not so limited and other variations with will be apparent to one of ordinary skill in the art.

The present methods can also be used for selecting a treatment and/or determining a treatment plan for a subject, based on the expression levels of a gene set (e.g., those disclosed herein).

Expression levels and/or reference expression levels may be stored in a suitable data storage medium (e.g., a database) and are, thus, also available for future diagnoses. This also allows efficiently diagnosing prevalence for a disease because suitable reference results can be identified in the database once it has been confirmed (in the future) that the subject from which the corresponding reference sample was obtained did develop fibrosis of the allograft and/or experience allograft rejection.

As used herein a "database" comprises data collected (e.g., analyte and/or reference level information and/or patient information) on a suitable storage medium. Moreover, the database, may further comprise a database management system. The database management system is, preferably, a network-based, hierarchical or object-oriented database management system. More preferably, the database will be implemented as a distributed (federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative of renal allograft rejection risk. Thus, if an identical or similar data set can be identified in the data collection, the test data set will be associated with renal allograft rejection risk.

Consequently, the information obtained from the data collection can be used to diagnose an allograft recipient's risk for allograft loss or based on a test data set obtained from a subject. More preferably, the data collection comprises characteristic values of all analytes comprised by any one of the groups recited above.

The invention further provides for the communication of assay results or diagnoses or both to technicians, physicians or patients, for example. In certain embodiments, computers will be used to communicate assay results or diagnoses or both to interested parties, e.g., physicians and their patients.

In some embodiments, the method disclosed herein further comprise modifying the recipient's clinical record to identify the recipient as being at risk for developing ACR and/or allograft loss. The clinical record may be stored in any suitable data storage medium (e.g., a computer readable medium).

In some embodiments of the invention, a diagnosis based on the methods provided herein is communicated to the allograft recipient as soon as possible after the diagnosis is obtained. The diagnosis may be communicated to the recipient by the recipient's treating physician. Alternatively, the diagnosis may be sent to a recipient by email or communicated to the subject by phone. The diagnosis may be sent to a recipient by in the form of a report. A computer may be used to communicate the diagnosis by email or phone. In certain embodiments, the message containing results of a diagnostic test may be generated and delivered automatically to the recipient using a combination of computer hardware and software which will be familiar to artisans skilled in telecommunications.

Aspects of the present invention include computer program products for identifying a subject who has undergone a renal allograft and is at risk for acute rejection, wherein the computer program product, when loaded onto a computer, is configured to employ a gene expression result from a sample derived from the subject to determining whether a subject who has undergone a renal allograft is at risk for allograft rejection wherein the gene expression result comprises expression data for at least one gene signature set.

Also provided are reference expression profiles for a phenotype that is one of: (a) low risk for acute rejection; or (b) high risk; wherein the expression profile is recorded on a computer readable medium that is accessible by a user, e.g., in a user readable format. In certain embodiments, the expression profile includes. In certain embodiments, the expression profile is a profile for a phenotype that is low risk. In certain embodiments, the expression profile is a profile for a phenotype that is high risk.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information.

"Recorded" refers to a process for storing information on computer readable medium, using any such methods a known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention, e.g., to and from a user. One format for an output means ranks expression profiles possessing varying degrees of similarity to a reference expression profile. Such presentation provides a skilled artisan with a ranking of similarities and identifies the degree of similarity contained in the test expression profile.

The present invention is described below in examples which as intended to further describe the invention without limiting the scope thereof.

As described in the Examples, below, a molecular signature to predict development/progression of renal allograft acute cellular rejection was discovered. The data demonstrated the use of peripheral mRNA profiling for surveillance and to stratify patients at risk for fibrosis and graft loss, obviating the need for allograft biopsy, and identifying those who may benefit from early interventions to prevent chronic allograft loss.

In the examples below, the following materials and methods were used:

Example 1: MiSEQ Assay

1) Custom Assay (barcoded probesets for 9 gene panel including a housekeeping gene panel)
2) Illumina® TruSeq® RNA Sample Preparation Kit v2
3) QIAGEN RNeasy® Kit for extraction of high quality total RNA MiSEQ Experiments The total RNA will be extracted using QIAGEN RNeasy® Kit. The sequencing library will be generated using the Illumina® TruSeq® RNA Sample Preparation Kit v2 by following the manufacturer's protocol: briefly, polyA-containing mRNA will be first purified and fragmented from the total RNA. The first-strand cDNAs synthesis will be performed using random hexamer primers and reverse transcriptase and followed by the second strand cDNA synthesis. After the endrepair process which converts the overhangs into blunt ends of cDNAs, multiple indexing adapters will be added to the end of the double stranded cDNA and PCR will be performed to enrich the targets using the primer pairs specific for the gene panel and housekeeping genes. Finally the indexed libraries will validated, normalized and pooled for sequencing on the MiSEQ sequencer.

MiSEQ Data Processing

The raw RNAseq data generated by the MiSEQ sequencer will be processed by the following procedure: The reads with good quality will be first aligned to several human reference databases including hg19 human genome, exon, splicing junction and contamination database including ribosome and mitochondria RNA sequences using the BWA[1] alignment algorithm. After filtering reads that mapped to the contamination database, the reads that are uniquely aligned with a maximal 2 mis-matches to the desired amplicon (i.e. PCR product from the paired primers) regions will be then counted as expression level for the corresponding gene and further subjected to quantile normalization across samples after log 2 transformation using R statistical programs.

Example 2: Nanostring Assay

1) Custom CodeSet (barcoded probesets for the 9 gene panel including 3 housekeeping genes and negative controls provided by Nanostring).
2) nCounter® Master Kit including nCounter Cartridge, nCounter Plate Pack and nCounter Prep Pack.
3) QIAGEN RNeasy® Kit for extraction of high quality total RNA Nanostring Experiments:

Total RNA will be extracted using QIAGEN RNeasy® Kit by following the manufacturer's protocol; Barcode probes will be annealed to the total RNA in solution at 65° C. with the master kit. The capture probe will capture the target to be immobilized for data. After hybridization, the sample will be transferred to the nCounter Pre Station and probe/target will be immobilized on the nCounter Cartridge and the probes are then counted by nCounter Digital Analyzer.

mRNA Transcriptomic Data analysis

The raw count data from Nanostring analyzer will be processed using the following procedure: the raw count data will be first normalized to the count of the housekeeping genes and the mRNAs with counts lower than the median plus 3 standard deviation of the counts of negative controls will be filtered out. Due to data variation arising from the reagent lot, the count for each mRNA from different reagent lots will be calibrated by multiplying a factor of the ratio of the averaged counts of the samples on different reagent lots. The calibrated counts from different experimental batches will be further adjusted the ComBat package.

Example 3: qPCR Assay

1) Primer container (16 tubes with one qPCR assay per tube for 12 genes including the 9 gene-panel and 2 housekeeping genes (ACTB and GAPDH) and the control probe 18S ribosomal RNA). The assays will be ordered from LifeTech.
2) TaqMan® Universal Master Mix II: reagents for qPCR reactions
3) TaqMan® ARRAY 96-WELL PLATE 6×16
4) Agilent AffinityScript QPCR cDNA Synthesis Kit: for the highest efficiency conversion of RNA to cDNA and fully optimized for real-time quantitative PCR (QPCR) applications.

Total RNA will be extracted from the allograft biopsy samples using the Allprep kit (QIAGEN-ALLprep kit, Valencia, Calif. USA). cDNA will be synthesized using the AffinityScript RT kit with oligo dt primers (Agilent Inc. Santa Clara, Calif.). TaqMan qPCR assays for the 9 gene set, 2 housekeeping genes (ACTB, GAPDH) and 18S will be purchased from ABI Life Technology (Grand Island, N.Y.). qPCR experiments will be performed on cDNAs using the TAQMAN universal mix and PCR reactions will be monitored and acquired using an ABI7900HT system. Samples will be measured in triplicate. Cycle Times (CT) values for the prediction gene set as well as the 2 housing genes will be generated. The ΔCT value of each gene will be computed by subtracting the average CT value for the housekeeping genes from the CT value of each gene.

Example 4: Performance of the Assay on Transplant Patients

Study Population

Eighty adult renal transplant patients were studied using gene expression profiling to determine the presence of subclinical acute rejection on their biopsy. The recipients were predominantly male (80%) with a mean age of 49.7, ranging from 19 to 75. Recipient race was 55% white, 22.5% African American, 11.25% Asian, and 11.25% Hispanic. Donors were 40% living donor and 60% deceased donor. The average donor age was 41.5 years with a range from 3 to 75 years. Thirty percent of the patients received anti-IL-2 receptor blocker for induction, 27.5% received Thymoglobulin® anti-thymocyte globulin (trademark of Sanofi-Aventis), 27.5% received no induction and 0.5% received Campath-1H. All patients received prednisone, prograf and mycophenolate mofetil.

Methods 10 cc's of peripheral blood was taken from 80 renal transplant recipients post-transplant and stored in a Paxgene tube. Blood is stored in a 4° C. refrigerator; if the assay cannot be performed immediately then the assay can be performed the following day. If the blood is to be stored longer it should be stored at −80° C.

The MiSEQ assay was performed as described in Example 1 above.

Prediction Analysis

The expression data obtained from the MiSEQ assay is then entered in to the computer program product for monitoring a subject who has received an allograft for an acute rejection (AR) response that accompanies the kit. This computer program product, when loaded onto a computer, is configured to employ a gene expression result from the sample derived from each of the subjects to determine a score and provide this ACR score to the user in a user-readable format. The ACR score is based on probability scores derived from reference experiments from which the diagnostic reference ranges have been validated.

Negative for ACR: ACR probability score below 0.16

Positive for ACR: ACR probability score above 0.5

The results are shown in Tables 1 and 2 attached hereto.

The following results are based on quantitation of 7 of 9 genes by MiSEQ assay. The 7 genes are: ANXA5, TSC22D1, AP1M1, CLK1, EFTUD2, SENP6, and SENP7.

As shown in the Tables 1, of the 80 patients 28 patients have a score of 0.16 or less and 18 have a score of 0.5 or above. Thirty-two patients are in the intermediate range and therefore categorized as indeterminate.

Comparison with conventional diagnostic methods, specifically pathology shows that on biopsy only one of the 28 patients diagnosed as no ACR (Group 1) by peripheral blood analysis has any evidence of acute rejection on biopsy (Table). However, this patient has BK nephropathy which causes inflammation on the biopsy from other causes. Patients with this diagnosis are over immunosuppressed and have a different peripheral blood profile than ACR. This data shows that BK inflammation can be differentiated from ACR inflammation on peripheral blood using the claimed assay. Four of the 18 ACR patients were found to have no ACR on biopsy; however, 2 of these patients went on to have ACR, thus the assay correctly identified them as high risk.

Of the 32 patients that are intermediate (Group 2) 11 patient are found to have biopsies that are suspicious (n=7) or ACR (n=4).

Of the 18 patients diagnosed with ACR (Group 3) 4 were diagnosed as having no ACR but 2 of these patients went on to have ACR at a later time point.

Using a reference range based on these results the assay has a sensitivity and specificity of 1 and 0.875 respectively with an NPV and a PPV of 1 and 0.78, respectively.

Management of Patients

1. Patients group 1 (ACR score negative), continue with the standard immunosuppression tapering protocol whereby patients are reduced to prednisone 5 mg if patients are still taking it, the prograf target level is reduced to 5-7 mg/dl and mycophenolate mofetil.
2. Patient group 2 (ACR indeterminate), the approach will be determined by the treating physician. Potential approaches include:
   a. Immunsuppression will not be tapered further and patients will have ongoing monitoring and if they test becomes positive they will be treated.
   b. A biopsy will be performed to confirm or rule out the presence of ACR.
3. Patient group 3 (ACR score positive), patients will receive a short course of high dose steroids e.g. 500 mg Prednisone for 3 days. The assay will be repeated one week after the completion of the steroids to determine if the ACR profile is now normal. If it is not a biopsy may be warranted.

Example 5: Primers

The primer pairs for the 17 genes are as follows:

| Gene | Forward | Reverse |
|---|---|---|
| ANXA5 | CAATTTAGAGCAACTACTCCTTGCTGT (SEQ ID NO: 1) | TATTCGAAGTATACCTGCCTACCTTGC (SEQ ID NO: 2) |
| ANXA5 | ATGAAGCTCAAGTTGAACAAGATGCTC (SEQ ID NO: 3) | AGAACTTAAATGGGGACAGATGAAGA (SEQ ID NO: 4) |
| AP1M1 | GTTCGAGCTCATGTCCTACCGTCTCAA (SEQ ID NO: 5) | CCTTTGATATGGATCGAGTCGGTGATC (SEQ ID NO: 6) |
| AP1M1 | CCACAGCCGCATCGAGTACATGATCAA (SEQ ID NO: 7) | CAAAAGCCAGTTCAAGCGGCGGTCAA (SEQ ID NO: 8) |
| C1GALT1C1 | GCATGTGATGATGTATGGGGTATACCG (SEQ ID NO: 9) | GGGCATTTGGGCATATTTTCAATGATG (SEQ ID NO: 10) |
| C1GALT1C1 | CCTGAAATATGCTGGAGTATTTGCAGA (SEQ ID NO: 11) | TGCAGAAGATGCTGATGGAAAAGATG (SEQ ID NO: 12) |
| CCDC82 | CAATGACAGAAGAAGTTGAAGATGAAC (SEQ ID NO: 13) | AGAAACAGTGGAAAGAATTTTCAGGCG (SEQ ID NO: 14) |

-continued

| | | |
|---|---|---|
| CCDC82 | TTCTCTTTCAAATAGATTTCAGGCCTC (SEQ ID NO: 15) | TCAACCCTCACATTCAGGAATAATTTT (SEQ ID NO: 16) |
| CLK1 | GGACCTCTACCAAAACATATGATACAG (SEQ ID NO: 17) | ATTTTCACCACGATCGATTAGACTGGG (SEQ ID NO: 18) |
| CLK1 | TCTGACTACACAGAGGCGTATAATCCC (SEQ ID NO: 19) | TGATGAACGCACCTTAATAAATCCAGA (SEQ ID NO: 20) |
| EFTUD2 | AATTCATGATCAAAACCCGCCGTAGG (SEQ ID NO: 21) | GAGCATCAGCAAATTCTTCGATGATCC (SEQ ID NO: 22) |
| EFTUD2 | AACCATAACCGAACCCCGAGGCAATGA (SEQ ID NO: 23) | GACCCTTGAAGTTCAATACCACATCTG (SEQ ID NO: 24) |
| ETAA1 | TGGGAAAACTTACTAGGTAGTGAACCT (SEQ ID NO: 25) | AAATATCGACATGCCTGAACTCTTTCC (SEQ ID NO: 26) |
| ETAA1 | AGTAACCCAAATCAGACTAGTGCATCA (SEQ ID NO: 27) | TCTTTGATGATTGGAATGATCCCTCAT (SEQ ID NO: 28) |
| F13A1 | CCAATTTGATGCACCTTTTGTTTTTGC (SEQ ID NO: 29) | GCGACCTCATTTACATTACAGCTAAGA (SEQ ID NO: 30) |
| F13A1 | TGGAGTAACAAGACCAATGAAGAAGATG SEQ ID NO: 31) | AACTCCACCGTGCAGTGGGAAGAAGT (SEQ ID NO: 32) |
| MAP1A | GAAAAAGACAAGGCCCTGGAACAGAA (SEQ ID NO: 33) | AAGATTCCAGAAGAGAAAGACAAAGCC (SEQ ID NO: 34) |
| MAP1A | CTGAAGGCAGAGAAGCGAAAGCTGAT (SEQ ID NO: 35) | CAAGGTAGGGAAAAAGCACCTTAAAGA (SEQ ID NO: 36) |
| NFYB | CCTCTGAAATTATACCTTCAGAAATTCAG (SEQ ID NO: 37) | CTATGAAAGGAGAAAAGGGAATTGGTGG (SEQ ID NO: 38) |
| NFYB | TGTTATGGTTTACACAACATCATATCAAC (SEQ ID NO: 39) | TCTGGTGTTCAGCAAATTCAGTTTTCA (SEQ ID NO: 40) |
| SENP6 | GGCATTTAAAGCCTACTATCTGTAAAC (SEQ ID NO: 41) | TATCCTACTTATGGACTCACTCCGAGG (SEQ ID NO: 42) |
| SENP6 | TGAGAAGGATTTTATTTTTGTACCCCT (SEQ ID NO: 43) | CACTGGTTTTTGGCTGTTGTTTGTTTC (SEQ ID NO: 44) |
| SENP7 | GACACTGTCTTTGAGTGCAGAGGATT (SEQ ID NO: 45) | GTACCGAGTCGAATATGTCAGTACCAA (SEQ ID NO: 46) |
| SENP7 | ATTAGAACACTCTGTATTAAGCCAGCA (SEQ ID NO: 47) | TCATTTTCCTTGAACTACACAATCCTG (SEQ ID NO: 48) |
| SPCS3 | TTATTCCATTTGTCTTAGGAAGGCCCA (SEQ ID NO: 49) | TTACATGTGACTAGCAACTTTCTCCAC (SEQ ID NO: 50) |
| SPCS3 | GTCAAAGCTTAAAAAATCAGGTGTGTCC (SEQ ID NO: 51) | GATAAGCCTGCAGTCTTAACCAGACCT (SEQ ID NO: 52) |
| TSC22D1 | ACTGTGCCTCTTTCTTCTCAAACAATG (SEQ ID NO: 53) | TGAGAGTGACAAAATGGTGACAGGTAG (SEQ ID NO: 54) |
| TSC22D1 | TCACCCATTTCATTGCTCGCTGCGAAA (SEQ ID NO: 55) | GTGAGACTGACATATGCCATTATCTCT (SEQ ID NO: 56) |
| TUBB1 | GTTCTGTCTATCCACCAGCTGATTGAG (SEQ ID NO: 57) | ATGCCTGTTTCTGCATTGACAATGAGG (SEQ ID NO: 58) |
| TUBB1 | AATACCTGGTCCAAACAAGAAAAACAA (SEQ ID NO: 59) | GACAAGCAAAACTAAAGAACTGCAGTC (SEQ ID NO: 60) |
| ZMAT1 | ACCTAGTCATTCAAAGTAGAAACCCAC (SEQ ID NO: 61) | TGCTTTCAGCTTTTATCCTGAGAGTGG (SEQ ID NO: 62) |
| ZMAT1 | CACATGCAAGGAAGTGAACATCAAATT (SEQ ID NO: 63) | ATCTAGTGAAGAATTCAAGGAAGACAC (SEQ ID NO: 64) |
| ZNF493 | AGCCTTTAGTATTTTCTCAACCCCTAC (SEQ ID NO: 65) | TCACACTGAAGAGAAATCCCACAGATG (SEQ ID NO: 66) |
| ZNF493 | CAGTCCTCAACTCCTAGTAAACATAAT (SEQ ID NO: 67) | AAACCATACAACTGTGAAGAATGTGGC (SEQ ID NO: 68) |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims It is further to be understood that all values are approximate, and are provided for description. Patents, patent applications, publications, product descriptions, and protocols are cited throughout this application, the disclosures of which are incorporated herein by reference in their entireties for all purposes.

TABLE 1

| 7 genes mapped Array ID | prob | AR_3m_time_point | | | ANXA5 |
|---|---|---|---|---|---|
| P16637 | 0.017452 | 0 | | | TSC22D 1 |
| P6610 | 0.024695 | 0 | | | APIMI |
| P41684 | 0.035203 | 0 | | | CLK1 |
| P12351 | 0.036215 | 0 | | | EFTUD2 |
| P36378 | 0.039165 | 0 | | | SENP6 |
| P6485 | 0.041505 | 0 | | | SENP7 |
| P29934 | 0.049993 | 0 | | | |
| P12683 | 0.051149 | 0 | | | |
| P20741 | 0.052609 | 0 | | | |
| P18463 | 0.062466 | 0 | | | |
| P12673 | 0.067403 | 0 | | | |
| P29561 | 0.068859 | 0 | | | |
| P15313 | 0.0694 | 0 | | | |
| P17064 | 0.077704 | 0 | | | |
| P6646 | 0.084929 | 0 | | | |
| P21093 | 0.108601 | 0 | | | |
| P19792 | 0.116445 | 0 | | | |
| P30609 | 0.119677 | 0 | | | |
| P44056 | 0.120967 | 0 | | | |
| P15762 | 0.121857 | 0 | | | |
| P22987 | 0.123687 | 0 | | | |
| P27071 | 0.12519 | 0 | | | |
| P7764 | 0.128861 | 0 | | | |
| P24797 | 0.130973 | 0 | | | |
| P17145 | 0.146718 | 0 | | | |
| P8751 | 0.14781 | 0 | | | |
| P24369 | 0.160478 | 0 | Specificity | 0.875 | |
| P20891 | 0.168029 | 0 | NPV | 1 | |
| P18496 | 0.170695 | 0 | | | |
| P39362 | 0.175342 | 1 | | | |
| P14029 | 0.17648 | 1 | | | |
| P6491 | 0.181622 | 1 | | | |
| P8403 | 0.193804 | 0 | | | |
| P16828 | 0.199011 | 0 | | | |
| P19996 | 0.203301 | 0 | | | |
| P42810 | 0.206721 | 0 | | | |
| P36244 | 0.208747 | 1 | | | |
| P14212 | 0.220862 | 0 | | | |
| P14307 | 0.229719 | 0 | | | |
| P14768 | 0.232455 | 1 | | | |
| P12616 | 0.237291 | 0 | | | |
| P35866 | 0.249239 | 0 | | | |
| P16865 | 0.265036 | 0 | | | |
| P41082 | 0.300904 | 1 | | | |
| P33638 | 0.302312 | 1 | | | |
| P6650 | 0.308944 | 0 | | | |
| P15063 | 0.323717 | 0 | | | |
| P27250 | 0.331253 | 0 | | | |
| P28901 | 0.351753 | 0 | | | |
| P44124 | 0.353624 | 0 | | | |
| P36051 | 0.419688 | 0 | | | |
| P44629 | 0.424203 | 0 | | | |
| P21504 | 0.439369 | 0 | | | |
| P21990 | 0.449395 | 1 | | | |
| P39437 | 0.455526 | 1 | | | |
| P22526 | 0.457334 | 0 | | | |
| P43535 | 0.462036 | 1 | | | |
| P27398 | 0.463876 | 1 | | | |
| P20787 | 0.464346 | 1 | | | |
| P12599 | 0.474293 | 0 | | | |
| P35241 | 0.496918 | 0 | | | |
| P7145 | 0499596 | 0 | | | |
| P21279 | 0.524475 | 1 | Sensitivity | 1 | |
| P26670 | 0.591051 | 0 | PPV | 0.78 | |
| P20593 | 0.613555 | 1 | | | |
| P43146 | 0.615636 | 1 | | | |
| P41240 | 0.630852 | 0 | | | |
| P21968 | 0.63729 | 1 | | | |
| P14608 | 0.656409 | 1 | | | |
| P7149 | 0.686441 | 1 | | | |
| P34400 | 0.741234 | 0 | | | |
| P30944 | 0.766445 | 1 | | | |
| P21713 | 0.772967 | 1 | | | |
| P32937 | 0.78113 | 1 | | | |
| P6607 | 0.78321 | 1 | | | |
| P41626 | 0.797169 | 0 | | | |
| P43144 | 0.882298 | 1 | | | |
| P28942 | 0.920221 | 1 | | | |
| P44035 | 0.941066 | 1 | | | |
| P33263 | 0.945597 | 1 | | | |

TABLE 2

| Participants ID | Probability Score | ACR at M3 | BAFF ACR Type | Age | Gender | Race |
|---|---|---|---|---|---|---|
| 16637 | 0.017451688 | No | None | 41 | Male | Hispanic |
| 6610 | 0.024694693 | No | None | 28 | Male | White/Caucasian |
| 41684 | 0.035203116 | No | None | 32 | Male | White/Caucasian |
| 12351 | 0.036214623 | No | None | 29 | Male | Pacific Islander |
| 36378 | 0.039165316 | No | None | 62 | Male | Asian |
| 6485 | 0.041505122 | No | None | 68 | Female | Hispanic |
| 29934 | 0.049993206 | No | None | 47 | Male | Black or African American |
| 12683 | 0.051148938 | No | None | 69 | Male | White/Caucasian |
| 20741 | 0.052609243 | No | None | 58 | Female | Hispanic |
| 18463 | 0.062455375 | No | None | 37 | Female | Hispanic |
| 12673 | 0.067403192 | No | None | 68 | Male | White/Caucasian |
| 29561 | 0.068859041 | No | None | 70 | Female | White/Caucasian |
| 15313 | 0.069400299 | No | None | 41 | Female | Black or African American |
| 17064 | 0.077704169 | No | None | 72 | Female | Unknown or Not Reported |
| 6646 | 0.084929087 | No | None | 41 | Female | White/Caucasian |
| 21093 | 0.108600537 | No | None | 28 | Male | Hispanic |
| 19792 | 0.116445383 | No | None | 40 | Female | White/Caucasian |
| 30609 | 0.119676671 | No | None | 42 | Female | White/Caucasian |
| 44056 | 0.120967164 | No | None | 66 | Male | Asian |

TABLE 2-continued

| | | | | | | |
|---|---|---|---|---|---|---|
| 15762 | 0.9121856593 | No | None | 61 | Male | Black or African American |
| 22987 | 0.123686939 | No | None | 61 | Male | White/Caucasian |
| 27071 | 0.125189794 | No | None | 21 | Female | White/Caucasian |
| 7764 | 0.128860617 | No | None | 63 | Male | Black or African American |
| 24797 | 0.130973269 | No | None | 54 | Male | White/Caucasian |
| 17145 | 0.146717843 | No | None | 66 | Female | Black or African American |
| 8751 | 0.147809602 | No | None | 65 | Male | Black or African American |
| 24369 | 0.160477933 | No | None | 29.8 | Female | White/Caucasian |
| 20891 | 0.168028954 | No | None | 43 | Male | Hispanic |
| 18496 | 0.170695322 | Yes | Suspicious | 31 | Female | Black or African American |
| 39362 | 0175341677 | Yes | 2A | 41 | Male | Black or African American |
| 14029 | 0.176479641 | Yes | 1B | 41 | Male | White/Caucasian |
| 6491 | 0.181621512 | No | None | 44 | Male | White/Caucasian |
| 8403 | 0.193804199 | No | None | 71 | Male | Hispanic |
| 16828 | 0.199010826 | No | None | 72 | Male | Black or African American |
| 19996 | 0.203301439 | No | None | 66 | Female | Black or African American |
| 42810 | 0.206720744 | No | None | 28 | Female | White/Caucasian |
| 36244 | 0.208764518 | Yes | Suspicious | 60 | Male | White/Caucasian |
| 14212 | 0.220862475 | No | None | 34 | Male | Asian |
| 14307 | 0.229719188 | No | None | 60 | Female | White/Caucasian |
| 14768 | 0.232454702 | Yes | 1A | 66 | Male | White/Caucasian |
| 12616 | 0.237291459 | No | None | 67 | Female | Hispanic |
| 35866 | 0.249239272 | No | None | 36 | Male | White/Caucasian |
| 16865 | 0.265036479 | No | None | 49 | Male | White/Caucasian |
| 41082 | 0.300903823 | Yes | Suspicious | 39 | Female | Pacific Islander |
| 33638 | 0.302311711 | Yes | Suspicious | 58 | Male | Black or African American |
| 6650 | 0.30894397 | No | None | 19 | Male | White/Caucasian |
| 15063 | 0.323717452 | No | None | 38 | Male | Black or African American |
| 27250 | 0.331253148 | No | None | 52 | Female | Black or African American |
| 28901 | 0.35175294 | No | None | 43 | Male | White/Caucasian |
| 44124 | 0.353624404 | No | None | 64 | Male | Pacific/Islander |
| 36051 | 0.419687549 | No | None | 65 | Male | White/Caucasian |
| 44629 | 0.424202859 | No | None | 47 | Male | White/Caucasian |
| 21504 | 0.439368688 | No | None | 59 | Female | White/Caucasian |
| 21990 | 0.449395338 | Yes | 1A | 58 | Male | White/Caucasian |
| 39437 | 0.455525639 | Yes | Suspicious | 61 | Male | Asian |
| 22526 | 0.457334127 | No | None | 41 | Male | Black or African American |
| 43535 | 0.462035743 | Yes | Suspicious | 29 | Female | Asian |
| 27398 | 0.463875597 | Yes | Suspicious | 37 | Female | White/Caucasian |
| 20787 | 0.464346411 | Yes | 1B | 67 | Female | Black or African American |
| 12599 | 0.474293044 | No | None | 63 | Male | Black or African American |
| 35241 | 0.496918307 | No | None | 65 | Male | White/Caucasian |
| 7145 | 0.499595501 | No | None | 50 | Male | Pacific/Islander |
| 21279 | 0.524475479 | Yes | Suspicious | 42 | Male | Black or African American |
| 26670 | 0.591050623 | No | None | 48 | Male | White/Caucasian |
| 20593 | 0.613554651 | Yes | 2A | 41 | Female | White/Caucasian |
| 43146 | 0.615635695 | Yes | 1A | 42 | Female | Asian |
| 41240 | 0.630852103 | No | None | 61 | Male | White/Caucasian |
| 21968 | 0.637290262 | Yes | Suspicious | 24 | Female | Hispanic |
| 14608 | 0.656408931 | Yes | Suspicious | 37 | Male | White/Caucasian |
| 7149 | 0.686440543 | Yes | Suspicious | 35 | Female | White/Caucasian |
| 34400 | 0.741234395 | No | None | 66 | Male | White/Caucasian |
| 30944 | 0.766444547 | Yes | Suspicious | 43.4 | Male | Asian |
| 21713 | 0.772966899 | Yes | 2A | 68 | Male | Asian |
| 32937 | 0.7311295 | Yes | Suspicious | 53 | Female | Black or African American |
| 6607 | 0.783210207 | Yes | Suspicious | 42 | Male | Asian |
| 41626 | 0.797168871 | No | None | 42 | Male | White/Caucasian |
| 43144 | 0.882297725 | Yes | Suspicious | 67 | Male | White/Caucasian |
| 28942 | 0.920220945 | Yes | Suspicious | 42 | Female | White/Caucasian |
| 44035 | 0.941065679 | Yes | Suspicious | 64 | Female | White/Caucasian |
| 33263 | 0.945596684 | Yes | Suspicious | 32 | Male | White/Caucasian |

| Donor Age | Donor Gender | Donor Race | Deceased/Living | Immunosuppression |
|---|---|---|---|---|
| 43 | Male | Hispanic | LURD | None |
| 52 | Male | White/Caucasian | LRD | None |
| 33 | Male | White/Caucasian | CadavericS | Basiliximab |
| 27 | Female | White. Caucasian | LURD | None |
| 63 | Female | Other | CadavericS | Thymoglobulin |
| 20 | Male | White/Caucasian | CadavericS | Basiliximab |
| 49 | Male | White/Caucasian | CadavericS | Basiliximab |
| 54 | Male | Hispanic | CadavericS | None |
| 43 | Female | Hispanic | LRD | Thymoglobulin |
| 35 | Male | Hispanic | LURD | None |
| 54 | Male | Hispanic | CadavericS | None |
| 48 | Female | White/Caucasian | LRD | None |
| 20 | Male | Black or African/ | LRD | Basiliximab |
| 69 | Male | White/Caucasian | CadavericS | Thymoglobulin |
| 26 | Female | White/Caucasian | CadavericS | None |
| 12 | Male | Hispanic | CadavericS | Campath-1 |

TABLE 2-continued

| | | | | |
|---|---|---|---|---|
| 42 | Female | White/Caucasian | LRD | None |
| 20 | Female | White/Caucasian | LURD | Thymoglobulin |
| 45 | Male | White/Caucasian | CadavericS | Thymoglobulin |
| 29 | Male | White/Caucasian | CadavericS | Thymoglobulin |
| 38 | Male | Black or African/ | CadavericS | Campath-1 |
| 16 | Female | White/Caucasian | CadavericS | Thymoglobulin |
| 44 | Female | White/Caucasian | CadavericS | None |
| 24 | Male | White/Caucasian | CadavericS | Campath-1 |
| 66 | Male | Black or African/ | LURD | Thymoglobulin |
| 68 | Female | White/Caucasian | CadavericS | Thymoglobulin |
| 37 | Female | White/Caucasian | CadavericS | Basiliximab |
| 35 | Male | Hispanic | LRD | None |
| 27 | Male | Black or African/ | CadavericS | Daclizumab |
| 20 | Male | White/Caucasian | CadavericS | Thymoglobulin |
| 24 | Female | White/Caucasian | CadavericS | Basiliximab |
| 17 | Male | White/Caucasian | CadavericS | Daclizumab |
| 16 | Female | White/Caucasian | CadavericS | None |
| 59 | Male | White/Caucasian | CadavericS | Campath-1 |
| 36 | Female | White/Caucasian | CadavericS | Thymoglobulin |
| 16 | Female | White/Caucasian | CadavericS | Basiliximab |
| 47 | Female | White/Caucasian | LRD | Basiliximab |
| 67 | Male | Asian | LRD | Basiliximab |
| 19 | Male | White/Caucasian | CadavericS | None |
| 65 | Female | White/Caucasian | LURD | Basiliximab |
| 55 | Female | White/Caucasian | CadavericS | Thymo/IVG |
| 22 | Female | White/Caucasian | CadavericS | None |
| 39 | Female | White/Caucasian | CadavericS | Campath-1 |
| 53 | Female | White/Caucasian | CadavericS | Basiliximab |
| 58 | Male | White/Caucasian | CadavericS | Basiliximab |
| 51 | Female | White/Caucasian | LRD | None |
| 3 | Female | White/Caucasian | CadavericS | Thymoglobulin |
| 41 | Male | White/Caucasian | CadavericS | Thymoglobulin32 |
| 32 | Female | White/Caucasian | CadavericS | Basiliximab |
| 63 | Male | White/Caucasian | CadavericS | Basiliximab |
| 56 | Male | White/Caucasian | LURD | None |
| 38 | Female | White/Caucasian | LRD | Basiliximab |
| 66 | Male | White/Caucasian | LURD | Basiliximab |
| 57 | Female | White/Caucasian | LURD | Basiliximab |
| 64 | Female | Asian | LURD | Basiliximab |
| 16 | Male | Hispanic | CadavericS | Campath-1 |
| 17 | Male | White/Caucasian | CadavericS | Basiliximab |
| 30 | Male | White/Caucasian | LURD | Basiliximab |
| 55 | Male | White/Caucasian | CadavericS | Thymoglobulin |
| 55 | Female | White/Caucasian | CadavericS | Thymoglobulin |
| 57 | Female | White/Caucasian | CadavericS | None |
| 39 | Female | White/Caucasian | CadavericS | None |
| 36 | Male | Black or African | LRD | Thymo/IVG |
| 9 | Male | White/Caucasian | CadavericS | None |
| 47 | Male | Black or African | CadavericS | Thymo/IVG |
| 30 | Male | White/Caucasian | CadavericS | Basiliximab |
| 57 | Male | White/Caucasian | CadavericS | Basiliximab |
| 48 | Female | Hispanic | CadavericS | Thymoglobulin |
| 34 | Female | White/Caucasian | CadavericS | Basiliximab |
| 64 | Male | White/Caucasian | CadavericS | Basiliximab |
| 63 | Male | White/Caucasian | LRD | Thymoglobulin |
| 44 | Female | Asian | LURD | None |
| 58 | Female | White/Caucasian | CadavericS | None |
| 50 | Male | Black or African | CadavericS | Thymoglobulin |
| 75 | Female | White/Caucasian | LURS | None |
| 42 | Female | White/Caucasian | LURD | Basiliximab |
| 65 | Female | White/Caucasian | LRD | Basiliximab |
| 30 | Female | White/Caucasian | LRD | Basiliximab |
| 52 | Male | White/Caucasian | CadavericS | Basiliximab |
| 26 | Female | White/Caucasian | LURD | Thymoglobulin |

What is claimed is:

1. A method for treating a renal allograft recipient at risk for allograft rejection, comprising the steps of:
    (a) determining a renal allograft recipient is at risk for allograft rejection, by performing the steps consisting of: (i) detecting expression levels of each of the genes of a preselected gene signature set in a blood specimen obtained from the allograft recipient, and (ii) determining that there are altered expression levels of at least one gene of the preselected gene signature set, compared to reference or control levels of the same genes; and
    (b) administering an anti-rejection drug or a high dose steroid to the allograft recipient determined to be at risk for allograft rejection,
    wherein the gene signature set consists of the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1.

2. The method of claim 1 wherein the anti-rejection drug is an immunosuppressive or anti-proliferative agent.

3. The method of claim 2 wherein the immunosuppressive agent is a member selected from the group consisting of a calcineurin inhibitor (CNI), mycophenolate mofetil (MMF), sirolimus, prednisone, Mycophenolate Sodium, Azathioprine and anti-thymocyte globulin.

4. The method of claim 3 wherein the CNI is cyclosporine or tacrolimus.

5. The method of claim 1 wherein the expression levels are detected by a method selected from the group consisting of Nanostring analysis, MiSEQ analysis, RNAseq and quantitative polymerase chain reaction (qPCR) analysis.

6. The method of claim 1 wherein said allograft rejection is subclinical rejection.

7. The method of claim 1 wherein said risk of allograft rejection is expressed as acute clinical rejection.

8. A method for treating a renal allograft recipient at risk for allograft rejection, comprising the steps of:
    (a) determining a renal allograft recipient is at risk for allograft rejection, by performing the steps consisting of: (i) detecting expression levels of each of the genes of a preselected gene signature set in a blood specimen obtained from the allograft recipient, and (ii) determining that there are altered expression levels of at least one gene of the preselected gene signature set, compared to reference or control levels of the same genes in a blood specimen isolated from an allograft recipient who did not suffer allograft loss; and
    (b) administering an anti-rejection drug or a high dose steroid to the allograft recipient determined to be at risk for allograft rejection,
    wherein the gene signature set consists of the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1.

9. The method of claim 8 wherein the anti-rejection drug is a member selected from the group consisting of a calcineurin inhibitor (CNI), mycophenolate mofetil (MMF), sirolimus, prednisone, Mycophenolate Sodium, Azathioprine and anti-thymocyte globulin.

10. The method of claim 9 wherein the CNI is cyclosporine or tacrolimus.

11. The method of claim 8 wherein said risk of allograft loss is expressed as subclinical rejection.

12. The method of claim 8 wherein said risk of allograft loss is expressed as acute clinical rejection.

13. A method for treating a renal allograft recipient at risk for acute cellular rejection, comprising the steps of:
    (a) determining a renal allograft recipient is at risk for acute cellular rejection, by performing the steps consisting of: (i) detecting expression levels of each of the genes of a preselected gene signature set in a blood specimen obtained from the allograft recipient, and (ii) determining that there are altered expression levels of at least one gene of the preselected signature set, compared to reference or control levels of the same genes in a blood specimen isolated from an allograft recipient who did not suffer acute cellular rejection; and (b) administering an anti-rejection drug or a high dose steroid to the allograft recipient determined to be at risk for acute cellular rejection, wherein the gene signature set consists of the genes SPCS3, ZMAT1, ETAA1, ZNF493, CCDC82, NFYB, F13A1, TUBB1, TSC22D1, SENP6, ANXA5, EFTUD2, SENP7, AP1M1, CLK1, MAP1A and C1GALT1C1.

* * * * *

SEQUENCE LISTING

<160> NUMBER OF SEQ ID NOS: 68

<210> SEQ ID NO 1
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 1
caatttagag caactactcc ttgctgt                                27

<210> SEQ ID NO 2
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 2
tattcgaagt atacctgcct accttgc                                27

<210> SEQ ID NO 3
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 3
atgaagctca agttgaacaa gatgctc                                27

<210> SEQ ID NO 4
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 4
agaacttaaa tgggggacag atgaaga                                27

<210> SEQ ID NO 5
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 5
gttcgagctc atgtcctacc gtctcaa                                27

<210> SEQ ID NO 6
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 6
cctttgatat ggatcgagtc ggtgatc                                27

<210> SEQ ID NO 7
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 7
ccacagccgc atcgagtaca tgatcaa                                27

<210> SEQ ID NO 8

```
<211> LENGTH: 26
<212> TYPE: DNA
<213> ORGANISM: Artificial Sequence
<220> FEATURE:
<223> OTHER INFORMATION: synthetically generated oligonucleotides

<400> SEQUENCE: 8
caaaagccag ttcaagcggc ggtcaa                                           26

<210> SEQ ID NO 9
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 9
gcatgtgatg atgtatgggg tataccg                                          27

<210> SEQ ID NO 10
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 10
gggcatttgg gcatattttc aatgatg                                          27

<210> SEQ ID NO 11
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 11
cctgaaatat gctggagtat ttgcaga                                          27

<210> SEQ ID NO 12
<211> LENGTH: 26
<212> TYPE: DNA
<213> ORGANISM: Artificial Sequence
<220> FEATURE:
<223> OTHER INFORMATION: synthetically generated oligonucleotides

<400> SEQUENCE: 12
tgcagaagat gctgatggaa aagatg                                           26

<210> SEQ ID NO 13
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 13
caatgacaga agaagttgaa gatgaac                                          27

<210> SEQ ID NO 14
<211> LENGTH: 27
<212> TYPE: DNA
<213> ORGANISM: Artificial Sequence
<220> FEATURE:
<223> OTHER INFORMATION: synthetically generated oligonucleotides
```

<400> SEQUENCE: 14
agaaacagtg gaaagaattt tcaggcg                                              27

<210> SEQ ID NO 15
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 15
ttctctttca aatagatttc aggcctc                                              27

<210> SEQ ID NO 16
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 16
tcaaccctca cattcaggaa taatttt                                              27

<210> SEQ ID NO 17
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 17
ggacctctac caaaacatat gatacag                                              27

<210> SEQ ID NO 18
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 18
attttcacca cgatcgatta gactggg                                              27

<210> SEQ ID NO 19
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 19
tctgactaca cagaggcgta taatccc                                              27

<210> SEQ ID NO 20
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 20
tgatgaacgc accttaataa atccaga                                              27

<210> SEQ ID NO 21

```
<211> LENGTH: 26
<212> TYPE: DNA
<213> ORGANISM: Artificial Sequence
<220> FEATURE:
<223> OTHER INFORMATION: synthetically generated oligonucleotides

<400> SEQUENCE: 21
aattcatgat caaacccgc cgtagg                                         26

<210> SEQ ID NO 22
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 22
gagcatcagc aaattcttcg atgatcc                                       27

<210> SEQ ID NO 23
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 23
aaccataacc gaaccccgag gcaatga                                       27

<210> SEQ ID NO 24
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 24
gacccttgaa gttcaatacc acatctg                                       27

<210> SEQ ID NO 25
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 25
tgggaaaact tactaggtag tgaacct                                       27

<210> SEQ ID NO 26
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 26
aaatatcgac atgcctgaac tctttcc                                       27

<210> SEQ ID NO 27
<211> LENGTH: 27
<212> TYPE: DNA
<213> ORGANISM: Artificial Sequence
<220> FEATURE:
<223> OTHER INFORMATION: synthetically generated oligonucleotides
```

<400> SEQUENCE: 27
agtaacccaa atcagactag tgcatca                                27

<210> SEQ ID NO 28
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 28
tctttgatga ttggaatgat ccctcat                                27

<210> SEQ ID NO 29
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 29
ccaatttgat gcacctttg tttttgc                                 27

<210> SEQ ID NO 30
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 30
gcgacctcat ttacattaca gctaaga                                27

<210> SEQ ID NO 31
<211> LENGTH: 28
<212> TYPE: DNA
<213> ORGANISM: Artificial Sequence
<220> FEATURE:
<223> OTHER INFORMATION: synthetically generated oligonucleotides

<400> SEQUENCE: 31
tggagtaaca agaccaatga agaagatg                               28

<210> SEQ ID NO 32
<211> LENGTH: 26
<212> TYPE: DNA
<213> ORGANISM: Artificial Sequence
<220> FEATURE:
<223> OTHER INFORMATION: synthetically generated oligonucleotides

<400> SEQUENCE: 32
aactccaccg tgcagtggga agaagt                                 26

<210> SEQ ID NO 33
<211> LENGTH: 26
<212> TYPE: DNA
<213> ORGANISM: Artificial Sequence
<220> FEATURE:
<223> OTHER INFORMATION: synthetically generated oligonucleotides

<400> SEQUENCE: 33
gaaaaagaca aggccctgga acagaa                                 26

<210> SEQ ID NO 34

<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 34
aagattccag aagagaaaga caaagcc                                        27

<210> SEQ ID NO 35
<211> LENGTH: 26
<212> TYPE: DNA
<213> ORGANISM: Artificial Sequence
<220> FEATURE:
<223> OTHER INFORMATION: synthetically generated oligonucleotides

<400> SEQUENCE: 35
ctgaaggcag agaagcgaaa gctgat                                         26

<210> SEQ ID NO 36
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 36
caaggtaggg aaaaagcacc ttaaaga                                        27

<210> SEQ ID NO 37
<211> LENGTH: 29
<212> TYPE: DNA
<213> ORGANISM: Artificial Sequence
<220> FEATURE:
<223> OTHER INFORMATION: synthetically generated oligonucleotides

<400> SEQUENCE: 37
cctctgaaat tataccttca gaaattcag                                      29

<210> SEQ ID NO 38
<211> LENGTH: 28
<212> TYPE: DNA
<213> ORGANISM: Artificial Sequence
<220> FEATURE:
<223> OTHER INFORMATION: synthetically generated oligonucleotides

<400> SEQUENCE: 38
ctatgaaagg agaaaaggga attggtgg                                       28

<210> SEQ ID NO 39
<211> LENGTH: 29
<212> TYPE: DNA
<213> ORGANISM: Artificial Sequence
<220> FEATURE:
<223> OTHER INFORMATION: synthetically generated oligonucleotides

<400> SEQUENCE: 39
tgttatggtt tacacaacat catatcaac                                      29

<210> SEQ ID NO 40
<211> LENGTH: 27
<212> TYPE: DNA
<213> ORGANISM: Artificial Sequence
<220> FEATURE:
<223> OTHER INFORMATION: synthetically generated oligonucleotides

```
<400> SEQUENCE: 40
tctggtgttc agcaaattca gttttca                                              27

<210> SEQ ID NO 41
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 41
ggcatttaaa gcctactatc tgtaaac                                              27

<210> SEQ ID NO 42
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 42
tatcctactt atggactcac tccgagg                                              27

<210> SEQ ID NO 43
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 43
tgagaaggat tttatttttg tacccct                                              27

<210> SEQ ID NO 44
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 44
cactggtttt tggctgttgt ttgtttc                                              27

<210> SEQ ID NO 45
<211> LENGTH: 26
<212> TYPE: DNA
<213> ORGANISM: Artificial Sequence
<220> FEATURE:
<223> OTHER INFORMATION: synthetically generated oligonucleotides

<400> SEQUENCE: 45
gacactgtct ttgagtgcag aggatt                                               26

<210> SEQ ID NO 46
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 46
gtaccgagtc gaatatgtca gtaccaa                                              27

<210> SEQ ID NO 47
```

<210> SEQ ID NO 47
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 47
attagaacac tctgtattaa gccagca                                            27

<210> SEQ ID NO 48
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 48
tcattttcct tgaactacac aatcctg                                            27

<210> SEQ ID NO 49
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 49
ttattccatt tgtcttagga aggccca                                            27

<210> SEQ ID NO 50
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 50
ttacatgtga ctagcaactt tctccac                                            27

<210> SEQ ID NO 51
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 51
gtcaaagctt aaaaatcagg tgtgtcc                                            27

<210> SEQ ID NO 52
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 52
gataagcctg cagtcttaac cagacct                                            27

<210> SEQ ID NO 53
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 53
actgtgcctc tttcttctca aacaatg                                              27

<210> SEQ ID NO 54
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 54
tgagagtgac aaaatggtga caggtag                                              27

<210> SEQ ID NO 55
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 55
tcacccattt cattgctcgc tgcgaaa                                              27

<210> SEQ ID NO 56
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 56
gtgagactga catatgccat tatctct                                              27

<210> SEQ ID NO 57
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 57
gttctgtcta tccaccagct gattgag                                              27

<210> SEQ ID NO 58
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 58
atgcctgttt ctgcattgac aatgagg                                              27

<210> SEQ ID NO 59
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 59
aatacctggt ccaaacaaga aaacaa                                               27

<210> SEQ ID NO 60

```
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 60
gacaagcaaa actaaagaac tgcagtc                                              27

<210> SEQ ID NO 61
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 61
acctagtcat tcaaagtaga aacccac                                              27

<210> SEQ ID NO 62
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 62
tgctttcagc ttttatcctg agagtgg                                              27

<210> SEQ ID NO 63
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 63
cacatgcaag gaagtgaaca tcaaatt                                              27

<210> SEQ ID NO 64
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 64
atctagtgaa gaattcaagg aagacac                                              27

<210> SEQ ID NO 65
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 65
agcctttagt attttctcaa cccctac                                              27

<210> SEQ ID NO 66
<211> LENGTH: 27
<212> TYPE: DNA
<213> ORGANISM: Artificial Sequence
<220> FEATURE:
<223> OTHER INFORMATION: synthetically generated oligonucleotides
```

```
<400> SEQUENCE: 66
tcacactgaa gagaaatccc acagatg                                                27

<210> SEQ ID NO 67
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 67
cagtcctcaa ctcctagtaa acataat                                                27

<210> SEQ ID NO 68
<211> LENGTH: 27
<212> TYPE: DNA
<213> ORGANISM: Artificial Sequence
<220> FEATURE:
<223> OTHER INFORMATION: synthetically generated oligonucleotides

<400> SEQUENCE: 68
aaaccataca actgtgaaga atgtggc                                                27
```